(12) United States Patent
Mihan et al.

(10) Patent No.: US 7,507,782 B2
(45) Date of Patent: Mar. 24, 2009

(54) TRANSITION-METAL COMPLEXES WITH TRIDENTATE, NITROGEN-CONTAINING LIGANDS

(75) Inventors: Shahram Mihan, Bad Soden (DE); Markus Enders, Heidelberg (DE); Olaf Fritz, Hirschhorn (DE)

(73) Assignee: Basell Polyolefine GmbH, Wesseling (DE)

(*) Notice: Subject to any disclaimer, the term of this patent is extended or adjusted under 35 U.S.C. 154(b) by 0 days.

(21) Appl. No.: 10/557,143

(22) PCT Filed: May 19, 2004

(86) PCT No.: PCT/EP2004/005373

§ 371 (c)(1),
(2), (4) Date: Feb. 12, 2007

(87) PCT Pub. No.: WO2004/104052

PCT Pub. Date: Dec. 2, 2004

(65) Prior Publication Data

US 2007/0185328 A1    Aug. 9, 2007

(30) Foreign Application Priority Data

May 21, 2003 (DE) ............................... 103 23 276

(51) Int. Cl.
C08F 4/69 (2006.01)
C08F 4/602 (2006.01)
C08F 4/74 (2006.01)
B01J 31/18 (2006.01)
B01J 31/22 (2006.01)

(52) U.S. Cl. .................. 526/161; 526/165; 502/103; 502/162; 502/167; 556/21; 556/42; 556/51; 556/57

(58) Field of Classification Search .............. 556/21, 556/42, 51, 57; 502/103, 162, 167; 526/161, 526/165

See application file for complete search history.

(56) References Cited

U.S. PATENT DOCUMENTS

| | | | |
|---|---|---|---|
| 3,242,150 A | 3/1966 | Scoggin et al. | 260/88.2 |
| 3,248,179 A | 4/1966 | Norwood | 23/285 |
| 6,337,297 B1 * | 1/2002 | Mimura et al. | 502/117 |
| 6,417,302 B1 | 7/2002 | Bohnen | 526/160 |
| 6,589,905 B1 | 7/2003 | Fischer et al. | 502/300 |
| 6,784,261 B1 | 8/2004 | Schopf et al. | 526/16 |
| 6,900,152 B2 * | 5/2005 | Yoshida et al. | 502/103 |
| 2002/0035029 A1 * | 3/2002 | Yoshida et al. | 502/154 |

FOREIGN PATENT DOCUMENTS

| | | |
|---|---|---|
| DE | 197 10 615 | 9/1998 |
| WO | WO 91/09882 | 7/1991 |
| WO | WO 96/00243 | 1/1996 |
| WO | WO 97/04015 | 2/1997 |
| WO | WO 97/36937 | 10/1997 |
| WO | WO 98/22486 | 5/1998 |
| WO | WO 98/27124 | 6/1998 |
| WO | WO 98/40419 | 9/1998 |
| WO | WO 99/06414 | 2/1999 |
| WO | WO 00/05277 | 2/2000 |
| WO | WO 00/24787 | 5/2000 |
| WO | WO 00/31090 | 6/2000 |
| WO | WO 01/09148 | 2/2001 |
| WO | WO 01/41920 | 6/2001 |

OTHER PUBLICATIONS

"8-Quinolylcyclopentadienyl, a Ligand with a Tailored Fit for Chelate Complexes", Chem. Ber. 129, pp. 459-463 (1996).
"Novel olefin polymerization catalysts based on iron and cobalt" J. Chem. Soc. Chem. Commun. 1998, pp. 849et seq.
"The Search for Larger anaad More Weakly Coordinating Anions", Chem. Rev. 93, pp. 927-947 (1993).
"Tris(pyridinealdoximato)metal Complexes as Ligands . . . ", Inorg. Chem. 40(28), pp. 6656-6665 (2001).
"An Easily Introduced and Removed Protecting Group for . . . ", J. Org. Chem. 45, pp. 4038-4040 (1980).
"Highly Active Iron and Cobalt Catalysts . . . ", J. Am. Chem. Soc., 120, pp. 4049-4050 (1998).
"Cyclopentadienyl compounds with nitrogen donors . . . ", J. Organomet. Chem. 500, pp. 175-185 (1995).
"ansa-Metallocene derivatives, XVII . . . ", J. Organomet. Chem. 369, pp. 359-370 (1989).
"Textbook of Organic Chemistry"—"Heterocycles", pp. 921-922, 931-933, 936-938, 941.
"Novel Chromium (III)Complexes . . . ", Organometallics 20, pp. 1247-1250 (2001).
"Phosphorylation of 1-Alkylmidazoled and . . . ", Heteroatom. Chem. 10(7), pp. 585-597 (1999).
S. Ross et al., "Tris(pyridinealdoximato)metal Complexes as Ligands for the Synthesis of Asymmetric Heterodinuclear $Cr^{III}M$ Species [M=Zn(II), Cu)(II), Ni(II), Fe(II), Mn(II), Cr(II), Co(III)]: A Magneto-Structural Study," Inorg. Chem., vol. 40(26), p. 6656-6665 (2001).

* cited by examiner

Primary Examiner—Caixia Lu
(74) Attorney, Agent, or Firm—Jarrod N. Raphael

(57) ABSTRACT

Transition metal complexes with tridentate, nitrogen-containing, uncharged ligand systems, a catalyst system comprising at least one of the transition metal complexes, the use of the catalyst system for the polymerization or copolymerization of olefins and a process for preparing polyolefins by polymerization or copolymerization of olefins in the presence of the catalyst system.

21 Claims, No Drawings

TRANSITION-METAL COMPLEXES WITH TRIDENTATE, NITROGEN-CONTAINING LIGANDS

The present invention relates to transition metal complexes with tridentate, nitrogen-containing, uncharged ligand systems and a catalyst system comprising at least one of the transition metal complexes.

In addition, the invention provides for the use of the catalyst system for the polymerization or copolymerization of olefins and provides a process for preparing polyolefins by polymerization or copolymerization of olefins in the presence of the catalyst system.

Catalyst systems having a uniquely defined active center, known as single site catalysts, are gaining increasing importance in the polymerization of olefins. These catalyst systems lead to polymers having narrow molecular weight distributions, which results in particularly favorable mechanical properties. Among these single site catalysts, metallocene catalysts have achieved particular industrial importance. In these, the polymer properties can be influenced by appropriate substituents on the cyclopentadienyl ligand. However, many metallocene catalysts can be obtained only via multistage syntheses and therefore represent a significant cost factor in olefin polymerization.

Heterocycles arid their various substituted derivatives are particularly easy to prepare and are therefore of particular interest as starting materials for a ligand synthesis. Substituted and unsubstituted tridentate ligand systems based on pyrazoles are often used as a type of cyclopentadienyl substitute. A particularly large number of complexes has been prepared using trispyrazolylborates of different types, with these ligands additionally having a negative charge. Thus, for example, (cyclopentadienyl)(trispyrazolyl) complexes of Ti and Zr are suitable catalysts for the polymerization of olefins.

Other complexes based on uncharged tridentate ligands which are built up from heterocycles have been studied to a lesser extent. Although many ligand systems are known, and are quite simple and inexpensive to prepare, only complexes of the late transition metals have hitherto been synthesized therewith. However, many of these late transition metal complexes serve mainly as model substances for enzymes and the suitability of the corresponding complexes of the early transition metals is not well known.

Tridentate imidazole complexes of chromium in which three (N-methylimidazole) units are linked in the 2 position via a $COCH_3$ bridge have been disclosed by Ruether, Thomas; Braussaud, Nathalie; Cavell, Kingsley J. in Organometallics (2001), 20(6), 1247-1250. However, only oligomers of ethylene can be obtained using this complex in the presence of methylaluminoxane.

It is an object of the present invention to find further transition metal complexes based on cyclopentadienyl ligands having a bridged donor which are suitable for the polymerization of olefins.

We have found that this object is achieved by transition metal complexes comprising the following structural feature of the formula (Z)M (I), where the variables have the following meanings:

M is a transition metal of group 3, 4, 5 or 6 of the Periodic Table of the Elements and Z is a ligand of the formula (II)

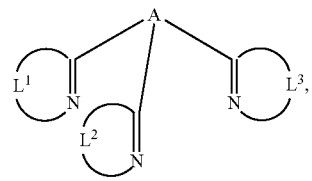

(II)

where
A is $CR^1$, $SiR^1$ or P,
$R^1$ is hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $NR^9_2$, $N(SiR^9_3)_2$, OH, $OSiR^9_3$, $SiR^9_3$ or halogen,
$L^1$-$L^3$ are each, independently of one another,

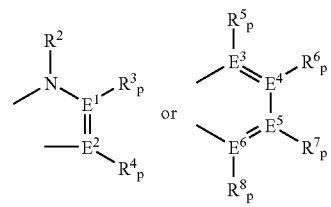

where
$E^1$-$E^6$ are each carbon or nitrogen,
p is 0 when $E^1$-$E^6$ is nitrogen and is 1 when $E^1$-$E^6$ is carbon,
$R^2$-$R^8$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $NR^9_2$, $N(SiR^9_3)_2$, $OR^9$, $OSiR^9_3$, $SiR^9_3$ or halogen, where the organic radicals $R^2$-$R^8$ may also be substituted by halogens and two vicinal radicals $R^2$-$R^8$ may also be joined to form a five- or six-membered ring and/or two vicinal radicals $R^2$-$R^8$ may be joined to form a heterocycle containing at least one atom from the group consisting of N, P, O and S, and
$R^9$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part and two geminal radicals $R^9$ may also be joined to form a five- or six-membered ring.

Furthermore, we have found a catalyst system comprising the transition metal complexes of the invention, the use of the transition metal complexes or the catalyst system for the polymerization or copolymerization of olefins and a process for preparing polyolefins by polymerization or copolymerization of olefins in the presence of the transition metal complex or the catalyst system and also polymers obtainable in this way.

The transition metal complexes of the present invention comprise the structural element of the formula (Z)M (I), where the variables have the above meanings. Further ligands may be bound to the metal atom M. The number of further ligands depends, for example, on the oxidation state of the metal atom. Possible ligands are ligands which are not cyclopentadienyl systems. Monoanionic and dianionic ligands as are described by way of example for X are suitable. In addition, Lewis bases such as amines, ethers, ketones, aldehydes, esters, sulfides or phosphines may also be bound to the metal center M.

M is a transition metal selected from the group consisting of scandium, yttrium, lanthanum, titanium, zirconium, hafnium, vanadium, niobium, tantalum, chromium, molybdenum and tungsten. Preference is given to titanium, zirconium, hafnium, vanadium or chromium, in particular vanadium or chromium. The transition metals are preferably present in the oxidation states 2, 3 and 4, in particular 3 and 4.

Z is a tridentate, uncharged ligand system which may bear any substituents and/or be fused with one or more aromatic, aliphatic, heterocyclic or heteroaromatic rings. 1, 2 or 3 nitrogen atoms of the C=N-L groups may be bound to the transition metal center. Preference is given to all three C=N groups being bound via the nitrogen to a transition metal center. The transition metal complexes of the present invention can be monomeric, dimeric, trimeric or oligomeric. Preference is given to monomeric transition metal complexes.

The groups —C=N-$L^1$, —C=N-$L^2$ and —C=N-$L^3$ are five- or six-membered heteroaromatics. In the case of five-member heteroaromatics, these contain at least two nitrogen atoms and may contain three, four or five nitrogen atoms and preferably contain two nitrogen atoms. In the case of six-membered heteroaromatics, these contain at least one nitrogen atom and may contain two, three, four, five or six nitrogen atoms and preferably contain one or two nitrogen atoms. Examples of five-membered heteroaromatics are imidazole, 1,2,3-triazole or 1,2,4-triazole. Examples of six-membered heteroaromatics are pyridine, pyridazine, pyrimidine, pyrazine, 1,3,5-triazine, 1,2,4-triazine and 1,2,3-triazine.

The five- and six-membered heteroaromatics are in each case linked to A as shown in the formula (I). Examples of five-membered heteroaromatics with indication of the point of linkage are 2-imidazolyl, 4-imidazolyl, 4-1,2,3-triazolyl, 3-1,2,4-triazolyl or 5-1,2,4triazolyl. Examples of six-membered heteroaromatics with indication of the point of linkage are 2-pyridinyl, 3-pyridazinyl, 2-pyrimidinyl, 4-pyrimidinyl, 2-pyrazinyl, 1,3,5-triazin-2-yl, 1,2,4-triazin-3-yl, 1,2,4-triazin-5-yl and 1,2,4-triazin-6-yl.

The polymerization behavior of the transition metal complexes of the present invention can be influenced by varying the substituents $R^2$-$R^8$. The type and number of the substituents can influence access of the olefins to be polymerized to the transition metal atom M or modify the bond angle of the ligand Z Thus, it is possible to modify the activity and selectivity of the catalyst in respect of various monomers, in particular bulky monomers. Since the substituents can also influence the rate of termination reactions of the growing polymer chain, the molecular weight of the polymers formed can also be altered in this way. The chemical structure of the substituents $R^2$ to $R^8$ can therefore be varied within a wide range in order to achieve the desired results and obtain a tailored catalyst system. The five- and six-membered heteroaromatics can, for example, be substituted by $C_1$-$C_{20}$-alkyl, $C_6$-$C_{20}$-aryl, alkylaryl having from 1 to 10 carbon atoms in the alkyl part and 6-10 carbon atoms in the aryl part, trialkylsilyl or halogens such as fluorine, chlorine or bromine, dialkylamide, alkylarylamide, diarylamide, alkoxy or aryloxy or be fused with one or more aromatics or heteroaromatics. Examples of carboorganic substituents $R^2$-$R^8$ are: $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may bear further alkyl groups as substituents, e.g. phenyl, naphthyl, biphenyl, anthranyl, o-, m-, p-methylphenyl, 2,3-, 2,4-, 2,5-, or 2,6-dimethylphenyl, 2,3,4-, 2,3,5-, 2,3,6-, 2,4,5-, 2,4,6- or 3,4,5-trimethylphenyl, or arylalkyl which may bear further alkyl groups as substituents, e.g. benzyl, o-, m-, p-methylbenzyl, 1- or 2-ethylphenyl, where two $R^2$ to $R^8$ may also be joined to form a 5- or 6-membered ring and the organic radicals $R^2$-$R^8$ may also be substituted by halogens such as fluorine, chlorine or bromine. $R^2$-$R^8$ may also be amino or alkoxy, for example dimethylamino, N-pyrrolidinyl, picolinyl, methoxy, ethoxy or isopropoxy. Possible radicals $R^9$ in organosilicon substituents $SiR^9_3$ are the same carboorganic radicals as have been described in detail above for $R^2$-$R^8$, where two $R^9$ may also be joined to form a 5- or 6-membered ring. Examples of suitable $SiR^9_3$ substituents are trimethylsilyl, triethylsilyl, butyldimethylsilyl, tributylsilyl, tri-tert-butylsilyl, triallylsilyl, triphenylsilyl or dimethylphenylsilyl. These $SiR^9_3$ radicals may also be bound via an oxygen or nitrogen atom, for example trimethylsilyloxy, triethylsilyloxy, butyldimethylsilyloxy, tributylsilyloxy or tri-tert-butylsilyloxy. Preferred radicals $R^2$-$R^8$ are hydrogen, methyl, ethyl, n-propyl, isopropyl, n-butyl, isobutyl, tert-butyl, n-pentyl, n-hexyl, n-heptyl, n-octyl, vinyl, allyl, benzyl, phenyl, ortho-dialkyl- or dichloro-substituted phenyls, trialkyl- or trichloro-substituted phenyls, naphthyl, biphenyl and anthranyl. Particularly useful organosilicon substituents are trialkylsilyl groups having from 1 to 10 carbon atoms in the alkyl radical, in particular trimethylsilyl groups.

Preference is also given to compounds in which two vicinal radicals $R^2$-$R^8$ form a cyclic fused ring system, i.e. together with $E^2$-$E^6$ form an unsubstituted or substituted benzoaromatic or heteroaromatic system. In this way, two vicinal radicals $R^2$-$R^8$ together with —C=N-$L^1$, —C=N-$L^2$ or —C=N-$L^3$ form a heteroaromatic system which is fused to a heteroaromatics or benzene. An example of a suitable benzo-fused five-membered heteroaromatic is benzimidazole. Examples of suitable benzo-fused six-membered heteroaromatics are quinoline, isoquinoline, phenanthridine, cinnoline, phthalazine, quinazoline or quinoxaline. An example of a suitable heteroaromatic-fused five-membered heteroaromatic is purine. Examples of suitable heteroaromatic-fused six-membered heteroaromatics are 1,8-naphthyridine, 1,5-naphthyridine, pteridine and 1,10-phenanthroline. Naming and numbering of the heterocycles has been taken from Lettau, Chemie der Heterocyclen, 1st Edition, VEB, Weinheim 1979. The heteroaromatics are preferably fused with the five- or six-membered heteroaromatics via a C—C double bond ($E^2$-$E^6$ is C). An example of a benzo-fused five-membered heteroaromatic, with indication of the point of linkage, is 2-benzimidazolyl. Examples of benzo-fused six-membered heteroaromatics with indication of the point of linkage are 2-quinolyl, 1-isoquinolyl, 3-isoquinolyl, 3-cinnolyl, 1-phthalazyl, 2-quinazolyl, 4-quinazolyl, 2-quinoxalyl, 1-phenanthridyl and 4-1,2,3-benzotriazinyl. The fused aromatic or heteroaromatic ring system may bear further $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $NR^9_2$, $N(SiR^9_3)_2$, $OR^9$, $OSiR^9_3$ or $SiR^9_3$ substituents.

$L^1$ to $L^3$ may be identical or different. Thus, five- and six-membered heteroaromatics containing different $L^1$ to $L^3$ can be present in Z. Z can also contain two or three different five-membered heteroaromatics or two or three different six-membered heteroaromatics. Preference is given to all three $L^1$ to $L^3$ being identical. Particular preference is given to $L^1$ to $L^3$ being identical and each forming a five-membered heteroaromatics system together with C=N.

The groups —C=N-$L^1$, —C=N-$L^2$ and —C=N-$L^3$ are linked to one another via A. A is $CR^1$, $SiR^1$ or P, where $R^1$ is hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $NR^9_2$, $N(SiR^9_3)_2$, OH, $OSiR^9_3$, $SiR^9_3$ or halogen. The polymerization behavior of the transition metal complexes of the present invention can be influenced by variation of the substituent $R^1$. Thus, the type of substituent can influence the arrangement of other substituents lined parallel to $R^1$ and thereby modify the bond angle of the ligand Z. The chemical structure of the substituent $R^1$ can be varied within a wide range. $R^1$ can, for example, be hydrogen, $C_1$-$C_{20}$-alkyl, $C_6$-$C_{20}$-aryl, alkylaryl having from 1 to 10 carbon atoms in the alkyl part and 6-10 carbon atoms in the aryl part, trialkylsilyl or halogen such as fluorine, chlorine or bromine, dialkylamide, alkylarylamide, diarylamide, hydroxy, siloxy or silyl. Examples of possible carboorganic substituents $R^1$ are: $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may bear further alkyl groups as substituents, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3, 6-, 2,4,5-, 2,4,6- or 3,4,5-trimethylphenyl, or arylalkyl which may bear further alkyl groups as substituents, e.g. benzyl, o-, m-, p-methylbenzyl, 1- or 2-ethylphenyl, where the organic radical $R^1$ may also be substituted by halogens such as fluorine, chlorine or bromine. Furthermore, $R^1$ can be amino or siloxy, for example dimethylamino, N-pyrrolidinyl, picolinyl, trimethylsiloxy, triethylsiloxy or triisopropylsiloxy. Possible radicals $R^9$ in organosilicon substituents $SiR^9_3$ are the same carboorganic radicals as mentioned in detail above for $R^2$-$R^8$, where two $R^9$ may also be joined to form a 5- or 6-membered ring. Examples of suitable substituents $SiR^9_3$ are trimethylsilyl, triethylsilyl, butyldimethylsilyl, tributylsilyl, tri-tert-butylsilyl, triallylsilyl, triphenylsilyl and dimethylphenylsilyl. These $SiR^9_3$ radicals may also be bound via an oxygen or nitrogen atom, for example trimethysilyloxy, triethylsilyloxy, butyldimethylsilyloxy, tributylsilyloxy or tri-tert-butylsilyloxy. Preferred radicals $R^1$ are relatively bulky since this favors polymerization over oligomerization and are $C_2$-$C_{20}$-alkyl, in particular branched $C_2$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, especially ethyl, n-propyl, isopropyl, n-butyl, isobutyl, tert-butyl, n-pentyl, n-hexyl, n-heptyl, n-octyl, vinyl, allyl, benzyl, phenyl, orthodialkyl- or ortho-dichloro-substituted phenyls, trialkyl- or trichloro-substituted phenyls, naphthyl, biphenyl and anthranyl. Particular preference is given to A being phosphorus.

Preferred transition metal complexes are ones in which M is $M^A$ and Z is $Z^A$ and which comprise the following structural feature of the formula $(Z^A)M^A$ (III), where the variables have the following meanings:

$M^A$ is a transition metal of group 3, 4, 5 or 6 of the Periodic Table of the Elements and $Z^A$ is a ligand of the formula (IV)

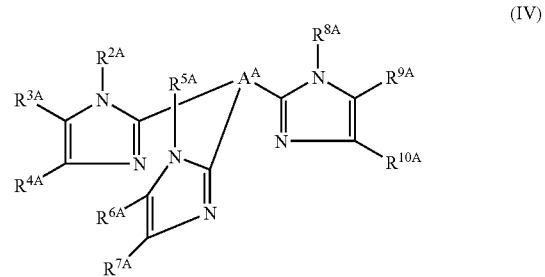

(IV)

where $A^A$ is $CR^{1A}$; $SiR^{1A}$ or P, $R^{1A}$ is hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $NR^{11A}_2$, $N(SiR^{11A}_3)_2$, OH, $OSiR^{11A}_3$, $SiR^{11A}_3$ or halogen, $R^{2A}$-$R^{10A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $NR^{11A}_2$, $N(SIR^{11A}_3)_2$, $OR^{11A}$, $OSiR^{11A}_3$, $SiR^{11A}_3$ or halogen, where the organic radicals $R^{2A}$-$R^{10A}$ may also be substituted by halogens and two vicinal radicals $R^{2A}$-$R^{10A}$ may also be joined to form a five- or six-membered ring, and/or two vicinal radicals $R^{2A}$-$R^{10A}$ may be joined to form a heterocycle containing at least one atom from the group consisting of N, P, O or S, and $R^{11A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part and two geminal radicals $R^{11A}$ may also be joined to form a five- or six-membered ring.

The preferred transition metal complexes comprise the structural element of the formula $(Z^A)M^A$ (III), where the variables are as defined above. Further ligands may be bound to the metal atom $M^A$. The number of further ligands depends, for example, on the oxidation state of the metal atom. Possible ligands are ligands which are not cyclopentadienyl systems. Monoanionic and dianionic ligands as are described by way of example for X are suitable. In addition, Lewis bases such as amines, ethers, ketones, aldehydes, esters, sulfides or phosphines may also be bound to the metal center $M^A$.

$M^A$ is a transition metal selected from the group consisting of scandium, yttrium, lanthanum, titanium, zirconium, hafnium, vanadium, niobium, tantalum, chromium, molybdenum and tungsten. Preference is given to titanium, zirconium, hafnium, vanadium or chromium, in particular titanium, vanadium or chromium. The transition metals are preferably present in the oxidation states 2, 3 and 4, in particular 3 and 4. Particular preference is given to chromium in the oxidation state 3.

$Z^A$ is a tridentate, uncharged ligand system comprising three imidazole systems linked in the 2 position via $A^A$. These imidazole systems may bear any substituents and/or be fused with one or more aromatic, aliphatic, heterocyclic or heteroaromatic rings. Z can be bound to the transition metal center via 1, 2 or 3 nitrogen atoms of the three imidazole groups (each having one C=N group per imidazole). Preference is given to all three C=N groups being bound via the nitrogen to the transition metal center $M^A$. The transition metal complexes of the present invention can be monomeric, dimeric, trimeric or oligomeric. Preference is given to monomeric transition metal complexes.

The polymerization behavior of the metal complexes can likewise be influenced by variation of the substituents $R^{2A}$-$R^{10A}$. Access of the olefins to be polymerized to the metal atom M can be influenced by the number and type of substituents. Thus, it is possible to modify the activity and selectivity of the catalyst in respect of various monomers, in particular bulky monomers. Since the substituents can also influence the rate of termination reactions of the growing polymer chain, the molecular weight of the polymers formed can also be altered in this way. The chemical structure of the substituents $R^{2A}$ to $R^{10A}$ can therefore be varied within a wide range in order to achieve the desired results and obtain a tailored catalyst system. Examples of carboorganic substituents $R^{2A}$-$R^{10A}$ are: $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may bear further alkyl groups as substituents, e.g. phenyl, naphthyl, biphenyl, anthranyl, o-, m-, p-methylphenyl, 2,3-, 2,4-, 2,5-, or 2,6-dimethylphenyl, 2,3,4-, 2,3,5-, 2,3,6-, 2,4,5-, 2,4,6- or 3,4,5-trimethylphenyl, or arylalkyl which may bear further alkyl groups as substituents, e.g. benzyl, o-, m-, p-methylbenzyl, 1- or 2-ethylphenyl, where two $R^{2A}$ to $R^{10A}$ may also be joined to form a 5- or 6-membered ring and the organic radicals $R^{2A}$-$R^{10A}$ may also be substituted by halogens such as fluorine, chlorine or bromine. Furthermore, $R^{2A}$-$R^{10A}$ can be amino or alkoxyl, for example dimethylamino, N-pyrrolidinyl, picolinyl, methoxy, ethoxy or isopropoxy. Possible radicals $R^{11A}$ in organosilicon substituents $SiR^{11A}_3$ are the same radicals as have been mentioned in detail above for $R^{2A}$-$R^{10A}$, where two $R^{11A}$ may also be joined to form a 5- or 6-membered ring. Examples of suitable substituents $SiR^{11A}_3$ are trimethylsilyl, triethylsilyl, butyldimethylsilyl, tributylsilyl, tri-tert-butylsilyl, triallylsilyl, triphenylsilyl and dimethylphenylsilyl. These $SiR^{11A}_3$ radicals can also be bound to the basic cyclopentadienyl skeleton via an oxygen or nitrogen atom, for example trimethylsilyloxy, triethylsilyloxy, butyldimethylsilyloxy, tributylsilyloxy or tri-tert-butylsilyloxy.

The radicals $R^{2A}$, $R^{5A}$ and $R^{8A}$ may be identical or different. Preference is given to $R^{2A}$, $R^{5A}$ and $R^{8A}$ being identical. The radicals $R^{2A}$, $R^{5A}$ and $R^{8A}$ are preferably each a linear or branched $C_1$-$C_{20}$-alkyl group such as methyl, ethyl, n-propyl, isopropyl, n-butyl, isobutyl, tert-butyl, n-pentyl, n-hexyl, n-heptyl or n-octyl or an arylalkyl group having 1-10 carbon atoms in the alkyl part and 6-20 carbon atoms in the aryl part, for example benzyl or ethylphenyl. The radicals $R^{3A}$, $R^{6A}$ and $R^{9A}$ may be identical or different. Preference is given to $R^{3A}$, $R^{6A}$ and $R^{9A}$ being identical. The radicals $R^{3A}$, $R^{6A}$ and $R^{9A}$ are preferably each $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl groups as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may bear further alkyl groups as substituents, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, or arylalkyl which may bear further alkyl groups as substituents, e.g. benzyl, o-, m-, p-methylbenzyl, 1- or 2-ethylphenyl, where the organic radicals $R^{3A}$, $R^{6A}$ and $R^{9A}$ may also be substituted by halogens such as fluorine, chlorine or bromine. In particular, $R^{3A}$, $R^{5A}$ and $R^{9A}$ are each hydrogen, methyl, ethyl, n-propyl, isopropyl, n-butyl, isobutyl, tert-butyl, n-pentyl, n-hexyl, n-heptyl, n-octyl, vinyl, allyl, benzyl, phenyl, ortho-dialkyl- or ortho-dichloro-substituted phenyls, trialkyl- or trichloro-substituted phenyls, naphthyl, biphenyl or anthranyl. The radicals $R^{4A}$, $R^{7A}$ and $R^{10A}$ may be Identical or different. Preference is given to $R^{4A}$, $R^{7A}$ and $R^{10A}$ being Identical. The preferred embodiments of the radicals $R^{4A}$, $R^{7A}$ and $R^{10A}$ are the same as have been described above for $R^{3A}$, $R^{6A}$ and $R^{9A}$. In a preferred embodiment, the members of the group of substituents $R^{2A}$, $R^{5A}$ and $R^{8A}$, the members of the group of substituents $R^{3A}$, $R^{6A}$ and $R^{9A}$ and the members of the group of substituents $R^{4A}$, $R^{7A}$ and $R^{10A}$ are in each case identical within the group. The individual groups can be identical to or different from one another.

In a further, preferred embodiment, pairs of vicinal radicals $R^{3A}$ and $R^{4A}$, $R^{6A}$ and $R^{7A}$ and $R^{9A}$ and $R^{10A}$ together with the carbon atoms to which they are bound in each case form an unsaturated or partially unsaturated 5- or 6-membered carbocyclic or heterocyclic ring. This heterocycle, preferably heteroaromatics, contains at least one atom from the group consisting of nitrogen, phosphorus, oxygen and sulfur, particularly preferably nitrogen and sulfur. These pairs of substituents particularly preferably each form a substituted or unsubstituted 6-membered aromatic.

In a further, preferred embodiment, at least one of the substituents $R^{4A}$, $R^{7A}$ and $R^{10A}$ is hydrogen, preferably all three substituents $R^{4A}$, $R^{7A}$ and $R^{10A}$ are hydrogen. This preferred embodiment is particularly preferable when M or $M^A$ is chromium. Substituents in this position seem to lower the activity of the chromium catalyst.

$A^A$ is $CR^{1A}$, $SiR^{1A}$ or P, where $R^{1A}$ is hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $NR^{11A}_2$, $N(SiR^{11A}_3)_2$, OH, $OSiR^{11A}_3$, $SiR^{11A}_3$ or halogen. $R^{1A}$ can be, for example, hydrogen, $C_1$-$C_{20}$-alkyl, $C_6$-$C_{20}$-aryl, alkylaryl having from 1 to 10 carbon atoms in the alkyl part and 6-10 carbon atoms in the aryl part, trialkylsilyl or halogens such as fluorine, chlorine or bromine, dialkylamide, alkylarylamide, diarylamide, hydroxy, siloxy or silyl. Examples of possible carboorganic substituents $R^{1A}$ are: $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may bear linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may bear further alkyl groups as substituents, e.g. phenyl, naphthyl, biphenyl, anthranyl, o-, m-, p-methylphenyl, 2,3-, 2,4-, 2,5-, or 2,6-dimethylphenyl, 2,3,4-, 2,3,5-, 2,3,6-, 2,4,5-, 2,4,6- or 3,4,5-trimethylphenyl, or arylalkyl which may bear further alkyl groups as substituents, e.g. benzyl, o-, m-, p-methylbenzyl, 1- or 2-ethylphenyl, where the organic radical $R^{1A}$ may also be substituted by halogens such as fluorine, chlorine or bromine. Furthermore, $R^{1A}$ can be amino or siloxy, for example dimethylamino, N-pyrrolidinyl, picolinyl, trimethylsiloxy, triethylsiloxy or triisopropylsiloxy. Possible radicals $R11^A$ in organosilicon substituents $SiR^{11A}_3$ are the same carboorganic radicals which have been described in detail above for $R^{2A}$-$R^{10A}$, where two $R^{11A}$ may also be joined to form a 5- or 6-membered ring. Examples of suitable substituents $SiR^{11A}_3$ are trimethylsilyl, triethylsilyl, butyldimethylsilyl, tributylsilyl, tri-tert-butylsilyl, triallylsilyl, triphenylsilyl and dimethylphenylsilyl. These $SiR^{11A}_3$ radicals may also be bound via an oxygen or nitrogen atom, for example trimethylsilyloxy, triethylsilyloxy, butyldimethylsilyloxy, tributylsilyloxy or tri-tert-butylsilyloxy. Preferred radicals $R^{1A}$ are hydrogen, methyl, ethyl, n-propyl, isopropyl, n-butyl, isobutyl, tert-butyl, n-pentyl, n-hexyl, n-heptyl, n-octyl, vinyl, allyl, benzyl, phenyl, ortho-dialkyl- or ortho-dichloro-substituted phenyls, trialkyl- or trichloro-substituted phenyls, naphthyl, biphenyl and anthranyl. Particular preference is given to $A^A$ being phosphorus.

Among the transition metal complexes of the present invention, preference is given to those of the formulae $(Z)MX_k$ (V) and $(Z^A)M^A X_k$ (VI) where the variables Z, M, $Z^A$ and $M^A$ are as defined above and their preferred embodiments are also preferred here and:

X are each, independently of one another, fluorine, chlorine, bromine, iodine, hydrogen, $C_1$-$C_{10}$-alkyl, $C_2$-$C_{10}$-alkenyl, $C_6$-$C_{20}$-aryl, alkylaryl having from 1-10 carbon atoms in the alkyl part and 6-20 carbon atoms in the aryl part, $NR^{1X}R^{2X}$, $OR^{1X}$, $SR^{1X}$, $SO_3R^{1X}$, $OC(O)R^{1X}$, CN, SCN, β-diketonate, CO, $BF_4^-$, $PF_6^-$ or a bulky noncoordinating anion, $R^{1X}$-$R^{2X}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{3X}_3$, where the organic radicals $R^{1X}$-$R^{2X}$ may also be substituted by halogens or nitrogen- and oxygen-containing groups and two radicals $R^{1X}$-$R^{2X}$ may also be joined to form a five- or six-membered ring, $R^{3X}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part and two radicals $R^{3X}$ may also be joined to form a five- or six-membered ring and k is 1, 2 or 3.

The embodiments and preferred embodiments described above for Z, M, $Z^A$ and $M^A$ also apply individually and in combination to these preferred transition metal complexes.

The ligands X are, for example, determined by the choice of the metal starting compounds used for the synthesis of the monocyclopentadienyl complexes, but can also be varied afterwards. Possible ligands X are, in particular, halogens such as fluorine, chlorine, bromine or iodine, in particular chlorine. Alkyl radicals such as methyl, ethyl, propyl, butyl, vinyl, allyl, phenyl or benzyl are also advantageous ligands X. As further ligands X, mention may be made, purely by way of example, and without any intention of being exhaustive, of trifluoroacetate, $BF_4^-$, $PF_6^-$ and weakly coordinating or non-coordinating anions (cf., for example, S. Strauss in Chem. Rev. 1993, 93, 927-942) such as $B(C_6F_5)_4^-$.

Amides, alkoxides, sulfonates, carboxylates and β-diketonates are also particularly useful ligands X. Variation of the radicals $R^{1X}$ and $R^{2X}$ enables fine adjustments to, for example, physical properties such as solubility to be made. Examples of possible carboorganic substituents $R^{1X}$-$R^{2X}$ are: $C_1$-$C_{20}$-alkyl which may be linear or branched, e.g. methyl, ethyl, n-propyl, isopropyl, n-butyl, iso-butyl, tert-butyl, n-pentyl, n-hexyl, n-heptyl, n-octyl, n-nonyl, n-decyl or n-dodecyl, 5 to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may bear further alkyl groups and/or N— or O-containing radicals as substituents, e.g. phenyl, naphthyl, biphenyl, anthranyl, o-, m-, p-methylphenyl, 2,3-, 2,4-, 2,5-, or 2,6-dimethylphenyl, 2,3,4-, 2,3, 5-, 2,3,6-, 2,4,5-, 2,4,6- or 3,4,5-trimethylphenyl, 2-methoxyphenyl, 2-N,N-dimethylaminophenyl or arylalkyl which may bear further alkyl groups as substituents, e.g. benzyl, o-, m-, p-methylbenzyl, 1- or 2-ethylphenyl, where $R^{1X}$ may also be joined to $R^{2X}$ to form a 5- or 6-membered ring and the organic radicals $R^{1X}$-$R^{2X}$ may also be substituted by halogens such as fluorine, chlorine or bromine. Possible radicals $R^{3X}$ in organosilicon substituents $SiR^{3X}_3$ are the same radicals as have been described in more detail above for $R^{1X}$-$R^{2X}$, where two $R^{3X}$ may also be joined to form a - or 6-membered ring. Examples of suitable substituents $SiR^{3X}_3$ are trimethylsilyl, triethylsilyl, butyldimethylsilyl, tributylsilyl, triallylsilyl, triphenylsilyl or dimethylphenylsilyl. Preference is given to using $C_1$-$C_{10}$-alkyl such as methyl, ethyl, n-propyl, n-butyl, tert-butyl, n-pentyl, n-hexyl, n-heptyl, n-octyl or vinyl, allyl, benzyl or phenyl as radicals $R^{1X}$ and $R^{2X}$. Some of these substituted ligands X are very particularly preferably used since they are obtainable from cheap and readily available starting materials. Thus, a particularly preferred embodiment is one in which X is dimethylamide, methoxide, ethoxide, isopropoxide, phenoxide, naphthoxide, triflate, p-toluenesulfonate, acetate or acetylacetonate.

The number k of ligands X depends on the oxidation state of the transition metal M or $M^A$. The number k can thus not be given in general terms. The oxidation states of the transition metals M or $M^A$ in catalytically active complexes are mostly known to those skilled in the art. Chromium, molybdenum and tungsten are very probably present in the oxidation state +3, and vanadium in the oxidation state +3 or +4. However, it is also possible to use complexes whose oxidation state does not correspond to that of the active catalyst. Such complexes can then be appropriately reduced or oxidized by means of suitable activators. Preference is given to using chromium complexes in the oxidation state +3 and titanium complexes in the oxidation state 3.

The synthesis of such ligand systems Z or $Z^A$ is described, for example, by N. J. Curtis and R. S. Brown in J. Org. Chem. 1980, 45, 4038-4040, and by A. A. Tolmachev, A. A. Yurchenko, A. S. Merculov, M. G. Semenova, E. V. Zarudnitskii, V. V. Ivanov and A. M. Pinchuk in Heteroatom. Chem. 1999, 10 (7), 585-597.

The metal complexes, in particular, the chromium complexes, can be obtained in a simple manner by reacting the appropriate ligands Z or ZA with metal salts such as metal chlorides, e.g. with chromium trichloride-tris(tetrahydrofuran), titanium trichloride-tris(tetrahydrofuran) or vanadium trichloride-tris(tetrahydrofuran).

The transition metal complexes of the present invention can be used either alone or together with further components as catalyst system for olefin polymerization. We have also found catalyst systems for olefin polymerization comprising A) at least one transition metal complex according to the present invention,
B) optionally, an organic or inorganic support,
C) optionally, one or more activating compounds,
D) optionally, one or more catalysts suitable for olefin polymerization and
E) optionally, one or more metal compounds containing a metal of group 1, 2 or 13 of the Periodic Table.

Thus, more than one of the transition metal complexes of the present invention can simultaneously be brought into contact with the olefin or olefins to be polymerized. This has the advantage that a wider range of polymers can be produced in this way. For example, bimodal products can be prepared in this way.

For the transition metal complexes of the present invention to be able to be used in polymerization processes in the gas phase or in suspension, it is often advantageous to use the complexes in the form of a solid, i.e. for them to be applied to a solid support B). Furthermore, the supported transition metal complexes have a high productivity. The transition metal complexes of the present invention can therefore also, if desired, be immobilized on an organic or inorganic support B) and used in supported form in the polymerization. This enables, for example, deposits in the reactor to be avoided and the polymer morphology to be controlled. As support materials, preference is given to using silica gel, magnesium chloride, aluminum oxide, mesoporous materials, aluminosilicates, hydrotalcites and organic polymers such as polyethylene, polypropylene, polystyrene, polytetrafluoroethylene or polar functionalized polymers, e.g. copolymers of ethene and acrylic esters, acrolein or vinyl acetate.

Particular preference is given to a catalyst system comprising a transition metal complex according to the present invention and at least one activating compound C) and also a support component B).

To obtain such a supported catalyst system, the unsupported catalyst system can be reacted with a support component B). The order in which the support component B), the transition metal complex A) of the present invention and the activating compound C) are combined is in principle immaterial. The transition metal complex A) of the present invention and the activating compound C) can be fixed to the support independently of one another or simultaneously. After the individual process steps, the solid can be washed with suitable inert solvents such as aliphatic or aromatic hydrocarbons.

In a preferred method of preparing the supported catalyst system, at least one of the transition metal complexes of the present invention is brought into contact with at least one activating compound C) in a suitable solvent, preferably giving a soluble reaction product, an adduct or a mixture. The preparation obtained in this way is then mixed with the dehydrated or passivated support material, the solvent is removed and the resulting supported transition metal complex catalyst system is dried to ensure that all or most of the solvent has been removed from the pores of the support material. The supported catalyst is obtained as a free-flowing powder. Examples of the industrial implementation of the above process are described in WO 96/00243, WO 98/40419 or WO 00/05277. A further preferred embodiment comprises firstly applying the activating compound C) to the support component B) and subsequently bringing this supported compound into contact with the transition metal complex A) of the present invention.

As support component B), preference is given to using finely divided supports which can be any organic or inorganic solids. In particular, the support component B) can be a porous support such as talc, a sheet silicate such as montmorillonite, mica, an inorganic oxide or a finely divided polymer powder (e.g. a polyolefin or a polymer having polar functional groups).

The support materials used preferably have a specific surface area in the range from 10 to 1 000 $m^2/g$, a pore volume in the range from 0.1 to 5 ml/g and a mean particle size of from 1 to 500 µm. Preference is given to supports having a specific surface area in the range from 50 to 700 $m^2/g$, a pore volume in the range from 0.4 to 3.5 ml/g and a mean particle size in the range from 5 to 350 µm. Particular preference is given to supports having a specific surface area in the range from 200 to 550 $m^2/g$, a pore volume in the range from 0.5 to 3.0 ml/g and a mean particle size of from 10 to 150 µm.

The inorganic support can be subjected to a thermal treatment, e.g. to remove adsorbed water. Such a drying treatment is generally carried out at from 80 to 300° C., preferably from 100 to 200° C. Drying at from 100 to 200° C. is preferably carried out under reduced pressure and/or under a blanket of inert gas (e.g. nitrogen), or the inorganic support can be calcined at from 200 to 1000° C. to produce the desired structure of the solid and/or the desired OH concentration on the surface. The support can also be treated chemically using customary desiccants such as metal alkyls, preferably aluminum alkyls, chlorosilanes or $SiCl_4$, or else methylaluminoxane. Appropriate treatment methods are described, for example, in WO 00/31090.

The inorganic support material can also be chemically modified. For example, the treatment of silica gel with $NH_4SiF_6$ or other fluorinating agents leads to fluorination of the silica gel surface, or treatment of silica gels with silanes containing nitrogen-, fluorine- or sulfur-containing groups leads to correspondingly modified silica gel surfaces.

Organic support materials such as finely divided polyolefin powders (e.g. polyethylene, polypropylene or polystyrene) can also be used and are preferably likewise freed of adhering moisture, solvent residues or other impurities by appropriate purification and drying operations before use. It is also possible to use functionalized polymer supports, e.g. ones based on polystyrene, polyethylene or polypropylene, via whose functional groups, for example ammonium or hydroxy groups, at least one of the catalyst components can be fixed.

Inorganic oxides suitable as support component B) may be found among the oxides of elements of groups 2, 3, 4, 5, 13, 14, 15 and 16 of the Periodic Table of the Elements. Examples of oxides preferred as supports include silicon dioxide, aluminum oxide and mixed oxides of the elements calcium, aluminum, silicon, magnesium or titanium and also corresponding oxide mixtures. Other inorganic oxides which can be used alone or in combination with the abovementioned preferred oxidic supports are, for example, MgO, CaO, $AlPO_4$, $ZrO_2$, $TiO_2$, $B_2O_3$ or mixtures thereof.

As solid support materials B) for catalysts for olefin polymerization, preference is given to using silica gels since particles whose size and structure make them suitable as supports for olefin polymerization can produced from this material. Spray-dried silica gels comprising spherical agglomerates of smaller granular particles, i.e. primary particles, have been found to be particularly useful. These silica gels can be dried and/or calcined before use.

Further preferred supports B) are hydrotalcites and calcined hydrotalcites. In mineralogy, hydrotalcite is a natural mineral having the ideal formula $$Mg_6Al_2(OH)_{16}CO_3 \cdot 4H_2O$$

whose structure is derived from that of brucite $Mg(OH)_2$. Brucite crystallizes in a sheet structure with the metal ions in octahedral holes between two layers of close-packed hydroxyl ions, with only every second layer of the octahedral holes being occupied. In hydrotalcite, some magnesium ions are replaced by aluminum ions, as a result of which the packet of layers gains a positive charge. This is compensated by the anions which are located together with water of crystallization in the layers in between.

Such sheet structures are found not only in magnesium-aluminum hydroxides, but also generally in mixed metal hydroxides of the formula $$M(II)_{2x}{}^{2+}M(III)_2{}^{3+}(OH)_{4x+4} \cdot A_{2/n}{}^{n-} \cdot zH_2O$$

which have a sheet structure and in which M(II) is a divalent metal such as Mg, Zn, Cu, Ni, Co, Mn, Ca and/or Fe and M(III) is a trivalent metal such as Al, Fe, Co, Mn, La, Ce and/or Cr, x is from 0.5 to 10 in steps of 0.5, A is an interstitial anion and n is the charge on the interstitial anion which can be from 1 to 8, usually from 1 to 4, and z is an integer from 1 to 6, in particular from 2 to 4. Possible interstitial anions are organic anions such as alkoxide anions, alkyl ether sulfates, aryl ether sulfates or glycol ether sulfates, inorganic anions such as, in particular, carbonate, hydrogencarbonate, nitrate, chloride, sulfate or $B(OH)_4{}^-$ or polyoxo metal anions such as $Mo_7O_{24}{}^{6-}$ or $V_{10}O_{28}{}^{6-}$. However, a mixture of a plurality of such anions can also be present.

Accordingly, all such mixed metal hydroxides having a sheet structure should be regarded as hydrotalcites for the purposes of the present invention.

Calcined hydrotalcites can be prepared from hydrotalcites by calcination, i.e. heating, by means of which the desired hydroxyl group content can be set. In addition, the crystal structure also changes. The preparation of the calcined hydrotalcites used according to the present invention is usually carried out at temperatures above 180° C. Preference is given to calcination for from 3 to 24 hours at from 250° C. to 1000° C., in particular from 400° C. to 700° C. It is possible for air or inert gas to be passed over the solid during calcination or for a vacuum to be applied.

On heating, the natural or synthetic hydrotalcites firstly give off water, i.e. drying occurs. On further heating, the actual calcination, the metal hydroxides are converted into the metal oxides by elimination of hydroxyl groups and interstitial anions; OH groups or interstitial anions such as carbonate can also still be present in the calcined hydrotalcites. A measure of this is the loss on ignition. This is the weight loss experienced by a sample which is heated in two steps firstly for 30 minutes at 200° C. in a drying oven and then for 1 hour at 950° C. in a muffle furnace.

The calcined hydrotalcites used as component B) are thus mixed oxides of the divalent and trivalent metals M(II) and M(III), with the molar ratio of M(II) to M(III) generally being in the range from 0.5 to 10, preferably from 0.75 to 8 and in particular from 1 to 4. Furthermore, normal amounts of impurities, for example Si, Fe, Na, Ca or Ti and also chlorides and sulfates, can also be present.

Preferred calcined hydrotalcites B) are mixed oxides in which M(II) is magnesium and M(III) is aluminum. Such aluminum-magnesium mixed oxides are obtainable from Condea Chemie GmbH (now Sasol Chemle), Hamburg, under the trade name Puralox Mg.

Preference is also given to calcined hydrotalcites in which the structural transformation is complete or virtually complete. Calcination, i.e. transformation of the structure, can be confirmed, for example, by means of X-ray diffraction patterns.

The hydrotalcites, calcined hydrotalcites or silica gels employed are generally used as finely divided powders having a mean particle diameter $d_{50}$ of from 5 to 200 μm, preferably from 10 to 150 μm, particularly preferably from 15 to 100 μm and in particular from 20 to 70 μm, and usually have pore volumes of from 0.1 to 10 cm$^3$/g, preferably from 0.2 to 5 cm$^3$/g, and specific surface areas of from 30 to 1000 m$^2$/g, preferably from 50 to 800 m$^2$/g and in particular from 100 to 600 m$^2$/g. The transition metal complexes of the present invention are preferably applied in such an amount that the concentration of transition metal complex in the finished catalyst system is from 5 to 200 μmol, preferably from 20 to 100 μmol and particularly preferably from 25 to 70 μmol per g of support B).

Some of the transition metal complexes of the present invention have little polymerization activity on their own and are then brought into contact with an activator, viz. the component C), to be able to display good polymerization activity. For this reason, the catalyst system optionally further comprises, as component C), one or more activating compounds, preferably at least one cation-forming compound C).

Suitable compounds C) which are able to react with the transition metal complex A) to convert it into a catalytically active, or more active, compound are, for example, compounds such as an aluminoxane, a strong uncharged Lewis acid, an ionic compound having a Lewis-acid cation or an ionic compound containing a Brönsted acid as cation.

As aluminoxanes, it is possible to use, for example, the compounds described in WO 00/31090. Particularly useful aluminoxanes are open-chain or cyclic aluminoxane compounds of the formula (X) or (XI)

(X)

(XI)

where $R^{1C}$-$R^{4C}$ are each, independently of one another, a $C_1$-$C_6$-alkyl group, preferably a methyl, ethyl, butyl or isobutyl group, and I is an integer from 1 to 30, preferably from 5 to 25.

A particularly useful aluminoxane compound is methylaluminoxane.

These oligomeric aluminoxane compounds are usually prepared by controlled reaction of a solution of trialkylaluminum with water. In general, the oligomeric aluminoxane compounds obtained in this way are in the form of mixtures of both linear and cyclic chain molecules of various lengths, so that I is to be regarded as a mean. The aluminoxane compounds can also be present in admixture with other metal alkyls, usually aluminum alkyls. Aluminoxane preparations suitable as component C) are commercially available.

Furthermore, modified aluminoxanes in which some of the hydrocarbon radicals have been replaced by hydrogen atoms or alkoxy, aryloxy, siloxy or amide radicals can also be used as component C) in place of the aluminoxane compounds of the formula (X) or (XI).

It has been found to be advantageous to use the transition metal complexes A) and the aluminoxane compounds in such amounts that the atomic ratio of aluminum from the aluminoxane compounds including any aluminum alkyl still present to the transition metal from the transition metal complex A) is in the range from 1:1 to 1000:1, preferably from 10:1 to 500:1 and in particular in the range from 20:1 to 400:1.

A further class of suitable activating components C) are hydroxyaluminoxanes. These can be prepared, for example, by addition of from 0.5 to 1.2 equivalents of water, preferably from 0.8 to 1.2 equivalents of water, per equivalent of aluminum to an alkylaluminum compound, in particular triisobutylaluminum, at low temperatures, usually below 0° C. Such compounds and their use in olefin polymerization are described, for example, in WO 00/24787. The atomic ratio of aluminum from the hydroxyaluminoxane compound to the transition metal from the transition metal complex A) is usually in the range from 1:1 to 100:1, preferably from 10:1 to 50:1 and in particular in the range from 20:1 to 40:1. Preference is given to using a transition metal dialkyl compound A).

As strong, uncharged Lewis acids, preference is given to compounds of the formula (XII)

$$M^{1C}X^{1C}X^{2C}X^{3C} \qquad \text{(XII)}$$

where $M^{1C}$ is an element of group 13 of the Periodic Table of the Elements, in particular B, Al or Ga, preferably B, $X^{1C}$, $X^{2C}$ and $X^{3C}$ are each hydrogen, $C_1$-$C_{10}$-alkyl, $C_6$-$C_{15}$-aryl, alkylaryl, arylalkyl, haloalkyl or haloaryl each having from 1 to 10 carbon atoms in the alkyl radical and from 6 to 20 carbon atoms in the aryl radical or fluorine, chlorine, bromine or Iodine, in particular haloaryls, preferably pentafluorophenyl.

Further examples of strong, uncharged Lewis acids are given in WO 00/31090.

Compounds of this type which are particularly useful as component C) are boranes and boroxins such as trialkylborane, triarylborane or trimethylboroxin. Particular preference is given to using boranes which bear at least two perfluorinated aryl radicals. Particular preference is given to compounds of the formula (XII) in which $X^{1C}$, $X^{2C}$ and $X^{3C}$ are identical, preferably tris(pentafluorophenyl)borane.

Suitable compounds C) are preferably prepared by reaction of aluminum or boron compounds of the formula (XII) with water, alcohols, phenol derivatives, thiophenol derivatives or aniline derivatives, with halogenated and especially perfluorinated alcohols and phenols being of particular importance. Examples of particularly useful compounds are pentafluorophenol, 1,1-bis(pentafluorophenyl)methanol and 4-hydroxy-2,2',3,3',4,4',5,5',6,6'-noafluorobiphenyl. Examples of combinations of compounds of the formula (XII) with Brönsted acids are, in particular, trimethylaluminum/pentafluorophenol, trimethylaluminum/1-bis(pentafluorophenyl) methanol, trimethylaluminum/4-hydroxy-2,2',3,3',4,4',5,5', 6,6'-nonafluorobiphenyl, triethylaluminum/ pentafluorophenol and triisobutylaluminum/ pentafluorophenol and triethylaluminum/4,4'-dihydroxy-2, 2',3,3',5,5',6,6'-octafluorobiphenyl hydrate.

In further suitable aluminum and boron compounds of the formula (XII), $X^{1C}$ is an OH group. Examples of compounds of this type are boronic acids and borinic acids, in particular borinic acids having perfluorinated aryl radicals, for example $(C_6F_5)_2$BOH.

Strong uncharged Lewis acids suitable as activating compounds C) also include the reaction products of a boronic acid with two equivalents of an aluminum trialkyl or the reaction products of an aluminum trialkyl with two equivalents of an acidic fluorinated, in particular perfluorinated, hydrocarbon compound such as pentafluorophenol or bis(pentafluorophenyl)borinic acid.

Suitable ionic compounds having Lewis-acid cations include salt-like compounds of the cation of the formula (XIII)

$$[((M^{2C})^{a+})Q_1Q_2\ldots Q_z]^{d+} \qquad \text{(XIII)}$$

where $M^{2C}$ is an element of groups 1 to 16 of the Periodic Table of the Elements, $Q_1$ to $Q_z$ are singly negatively charged groups such as $C_1$-$C_{28}$-alkyl, $C_6$-$C_{15}$-aryl, alkylaryl, arylalkyl, haloalkyl, haloaryl each having from 6 to 20 carbon atoms in the aryl radical and from 1 to 28 carbon atoms in the alkyl radical, $C_3$-$C_{10}$-cycloalkyl which may bear $C_1$-$C_{10}$-alkyl groups as substituents, halogen, $C_1$-$C_{28}$-alkoxy, $C_6$-$C_{15}$-aryloxy, silyl or mercaptyl groups, a is an integer from 1 to 6 and z is an integer from 0 to 5, d corresponds to the difference a–z, but d is greater than or equal to 1.

Particularly useful cations are carbonium cations, oxonium cations and sulfonium cations and also cationic transition metal complexes. Particular mention may be made of the triphenylmethyl cation, the silver cation and the 1,1'-dimethylferrocenyl cation. They preferably have noncoordinating counterions, in particular boron compounds as are also mentioned in WO 91/09882, preferably tetrakis(pentafluorophenyl)borate.

Salts having noncoordinating anions can also be prepared by combining a boron or aluminum compound, e.g. an aluminum alkyl, with a second compound which can react to link two or more boron or aluminum atoms, e.g. water, and a third compound which forms an ionizing ionic compound with the boron or aluminum compound, e.g. triphenylchloromethane, or optionally a base, preferably an organic nitrogen-containing base, for example an amine, an aniline derivative or a nitrogen heterocycle. In addition, a fourth compound which likewise reacts with the boron or aluminum compound, e.g. pentafluorophenol, can be added.

Ionic compounds containing Brönsted acids as cations preferably likewise have noncoordinating counterions. As Brönsted acid, particular preference is given to protonated amine or aniline derivatives. Preferred cations are N,N-dimethylanilinium, N,N-dimethylcyclohexylammonium and N,N-dimethylbenzylammonium and also derivatives of the latter two.

Compounds containing anionic boron heterocycles as are described in WO 9736937 are also suitable as component C), in particular dimethylanilinium boratabenzenes or trityl boratabenzenes.

Preferred ionic compounds C) contain borates which bear at least two perfluorinated aryl radicals. Particular preference is given to N,N-dimethylanilinium tetrakis(pentafluorophenyl)borate and in particular N,N-dimethylcyclohexylammonium tetrakis(pentafluorophenyl)borate, N,N-dimethylbenzylammonium tetrakis(pentafluorophenyl)borate or trityl tetrakispentafluorophenylborate.

It is also possible for two or more borate anions and/or boranes to be joined to one another or one borate anion to be joined to a borane, as in the dianion [(C$_6$F$_5$)$_3$B—C$_6$F$_4$—B(C$_6$F$_5$)$_3$]$^{2-}$ and the anion [(C$_6$F$_5$)$_3$B—CN—B(C$_6$F$_5$)$_3$]$^-$, or the borate anion can be bound via a bridge having a suitable functional group to the support surface.

Further suitable activating compounds C) are listed in WO 00/31090.

The amount of strong, uncharged Lewis acids, ionic compounds having Lewis-acid cations or ionic compounds containing Brönsted acids as cations is preferably from 0.1 to 20 equivalents, more preferably from 1 to 10 equivalents, based on the transition metal complex A).

Suitable activating compounds C) also include boron-aluminum compounds such as di[bis(pentafluorophenyl)boroxy]methylalane. Examples of such boron-aluminum compounds are those disclosed in WO 99/06414.

It is also possible to use mixtures of all the abovementioned activating compounds C). Preferred mixtures comprise aluminoxanes, in particular methylaluminoxane, and an ionic compound, in particular one containing the tetrakis(pentafluorophenyl)borate anion, and/or a strong uncharged Lewis acid, in particular tris(pentafluorophenyl)borane.

Both the transition metal complexes A) and the activating compounds C) are preferably used in a solvent, preferably an aromatic hydrocarbon having from 6 to 20 carbon atoms, in particular xylenes, toluene, pentane, hexane, heptane or a mixture thereof.

A further possibility is to use an activating compound C) which can simultaneously be employed as support B). Such systems are obtained, for example, from an inorganic oxide by treatment with zirconium alkoxide and subsequent chlorination, for example by means of carbon tetrachloride. The preparation of such systems is described, for example, in WO 01/41920.

A likewise broad product spectrum can be achieved by use of the transition metal complexes A) of the present invention in combination with at least one further catalyst D) which is suitable for the polymerization of olefins. It is therefore possible to use one or more catalysts suitable for olefin polymerization as optional component D) in the catalyst system. Possible catalysts D) are, in particular, classical Ziegler-Natta catalysts based on titanium and classical Phillips catalysts based on chromium oxides.

Possible components D) are in principle all compounds of transition metals of groups 3 to 12 of the Periodic Table or the lanthanides which contain organic groups and preferably form active catalysts for olefin polymerization after reaction with the components C) in the presence of A) and optionally B) and/or E). These are usually compounds in which at least one monodentate or polydentate ligand is bound to the central atom via a sigma or pi bond. Possible ligands include both ligands containing cyclopentadienyl groups and ligands which are free of cyclopentadienyl groups. A large number of such compounds B) suitable for olefin polymerization are described in Chem. Rev. 2000, Vol. 100, No. 4. Furthermore, multinuclear cyclopentadienyl complexes are also suitable for olefin polymerization.

Particularly well-suited components D) include compounds having at least one cyclopentadienyl ligand, which are generally referred to as metallocene complexes. Particularly useful metallocene complexes are those of the formula (XIV)

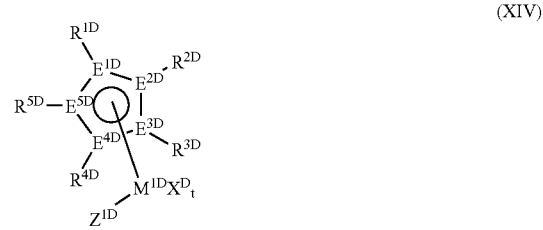

(XIV)

where the substituents and indices have the following meanings:

M$^{1D}$ is titanium, zirconium, hafnium, vanadium, niobium, tantalum, chromium, molybdenum or tungsten, or an element of group 3 of the Periodic Table and the lanthanides, X$^D$ is fluorine, chlorine, bromine, iodine, hydrogen, C$_1$-C$_{10}$-alkyl, C$_2$-C$_{10}$-alkenyl, C$_6$-C$_{15}$-aryl, alkylaryl having from 1 to 10 carbon atoms in the alkyl part and from 6 to 20 carbon atoms in the aryl part, —OR$^{6D}$ or —NR$^{6D}$R$^{7D}$, or two radicals X$^D$ form a substituted or unsubstituted diene ligand, in particular a 1,3-diene ligand, and the radicals X$^D$ are identical or different and may be joined to one another, E$^{1D}$-E$^{5D}$ are each carbon or not more than E$^{1D}$ to E$^{5D}$ is phosphorus or nitrogen, preferably carbon, t is 1, 2 or 3 and is such that, depending on the valence of M$^{1D}$, the metallocene complex of the formula (XIV) is uncharged, where R$^{6D}$ and R$^{7D}$ are each C$_1$-C$_{10}$-alkyl, C$_6$-C$_{15}$-aryl, alkylaryl, arylalkyl, fluoroalkyl or fluoroaryl each having from 1 to 10 carbon atoms in the alkyl radical and from 6 to 20 carbon atoms in the aryl radical, and R$^{1D}$ to R$^{5D}$ are each, independently of one another, hydrogen, C$_1$-C$_{22}$-alkyl, 5- to 7-membered cycloalkyl or cycloalkenyl which may in turn bear C$_1$-C$_{10}$-alkyl groups as substituents, C$_2$-C$_{22}$-alkenyl, C$_6$-C$_{22}$-aryl, arylalkyl having from 1 to 16 carbon atoms in the alkyl part and from 6 to 21 carbon atoms in the aryl part, NR$^{8D}$$_2$, N(SiR$^{8D}$$_3$)$_2$, OR$^{8D}$, OSiR$^{8D}$$_3$, SiR$^{8D}$$_3$, where the organic radicals R$^{1D}$-R$^{5D}$ may also be substituted by halogens and/or two radicals R$^{1D}$-R$^{5D}$, in particular vicinal radicals, may also be joined to form a five-, six- or seven-membered ring, and/or two vicinal radicals R$^{1D}$-R$^{5D}$ may be joined to form a five-, six- or seven-membered heterocycle which contains at least one atom from the group consisting of N, P, O and S, where R$^{8D}$ can be identical or different and are each C$_1$-C$_{10}$-alkyl, C$_3$-C$_{10}$-cycloalkyl, C$_6$-C$_{15}$-aryl, C$_1$-C$_4$-alkoxy or C$_6$-C$_{10}$-aryloxy and Z$^{1D}$ is as defined for X$^D$ or is

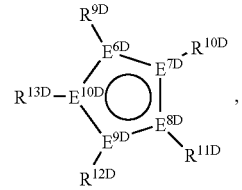

where the radicals $R^{9D}$ to $R^{13D}$ are each, independently of one another, hydrogen, $C_1$-$C_{22}$-alkyl, 5- to 7-membered cycloalkyl or cycloalkenyl which may in turn bear $C_1$-$C_{10}$-alkyl groups as substituents, $C_2$-$C_{22}$-alkenyl, $C_6$-$C_{22}$-aryl, arylalkyl having from 1 to 16 carbon atoms in the alkyl part and 6-21 carbon atoms in the aryl part, $NR^{14D}{}_2$, $N(SiR^{14D}{}_3)_2$, $OR^{14D}$, $OSiR^{14D}{}_3$, $SiR^{14D}{}_3$, where the organic radicals $R^{9D}$-$R^{13D}$ may also be substituted by halogens and/or two radicals $R^{9D}$-$R^{13D}$, in particular vicinal radicals, may also be joined to form a five-, six- or seven-membered ring, and/or two vicinal radicals $R^{9D}$-$R^{13D}$ may be joined to form a five-, six- or seven-membered heterocycle which contains at least one atom from the group consisting of N, P, O and S, where $R^{14D}$ are identical or different and are each $C_1$-$C_{10}$-alkyl, $C_3$-$C_{10}$-cycloalkyl, $C_6$-$C_{15}$-aryl, $C_1$-$C_4$-alkoxy or $C_6$-$C_{10}$-aryloxy, $E^{6D}$-$E^{10D}$ are each carbon or not more than one $E^{6D}$ to $E^{10D}$ is phosphorus or nitrogen, preferably carbon, or the radicals $R^{4D}$ and $Z^{1D}$ together form an —$R^{15D}{}_v$-$A^{1D}$- group in which $R^{15D}$ is

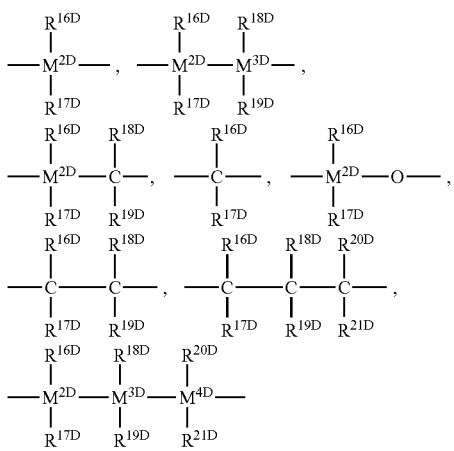

=$BR^{16D}$, =$BNR^{16D}R^{17D}$, =$AlR^{16D}$, —Ge—, —Sn—, —O—, —S—, =SO, =SO$_2$, =$NR^{16D}$, =CO, =$PR^{16D}$ or =$P(O)R^{16D}$, where $R^{16D}$-$R^{21D}$ are identical or different and are each a hydrogen atom, a halogen atom, a trimethylsilyl group, a $C_1$-$C_{10}$-alkyl group, a $C_1$-$C_{10}$-fluoroalkyl group, a $C_6$-$C_{10}$-fluoroaryl group, a $C_6$-$C_{10}$-aryl group, a $C_1$-$C_{10}$-alkoxy group, a $C_7$-$C_{15}$-alkylaryloxy group, a $C_2$-$C_{10}$-alkenyl group, a $C_7$-$C_{40}$-arylalkyl group, a $C_8$-$C_{40}$-arylalkenyl group or a $C_7$-$C_{40}$-alkylaryl group or two adjacent radicals together with the atoms connecting them form a saturated or unsaturated ring having from 4 to 15 carbon atoms, and $M^{2D}$-$M^{4D}$ is silicon, germanium or tin, preferably silicon, $A^{1D}$ is

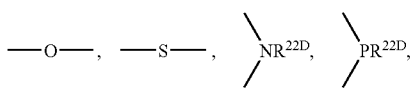

=O, =S, =$NR^{22D}$, —O—$R^{22D}$, —$NR^{22D}{}_2$, —$PR^{22D}{}_2$ or an unsubstituted, substituted or fused, heterocyclic ring system, where $R^{22D}$ are each, independently of one another, $C_1$-$C_{10}$-alkyl, $C_6$-$C_{15}$-aryl, $C_3$-$C_{10}$-cycloalkyl, $C_7$-$C_{18}$-alkylaryl or $Si(R^{23D})_3$, $R^{23D}$ is hydrogen, $C_1$-$C_{10}$-alkyl, $C_6$-$C_{15}$-aryl which may in turn bear $C_1$-$C_4$alkyl groups as substituents or $C_3$-$C_{10}$-cycloalkyl, v is 1 or when $A^{1D}$ is an unsubstituted, substituted or fused, heterocyclic ring system may also be 0, or the radicals $R^{4D}$ and $R^{12D}$ together form an —$R^{15D}$-group.

$A^{1D}$ together with the bridge $R^{15D}$ can, for example, form an amine, ether, thioether or phosphine. However, $A^{1D}$ may also be an unsubstituted, substituted or fused, heterocyclic aromatic ring system which can contain heteroatoms from the group consisting of oxygen, sulfur, nitrogen and phosphorus in addition to carbon atoms in the ring. Examples of five-membered heteroaryl groups which can contain from 1 to 4 nitrogen atoms and/or a sulfur or oxygen atom as ring atoms in addition to carbon atoms are 2-furyl, 2-thienyl, 2-pyrrolyl, 3-isoxazolyl, 5-isoxazolyl, 3-isothiazolyl, 5-isothiazolyl, 1-pyrazolyl, 3-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,3,4-oxadiazol-2-yl or 1,2,4triazol-3-yl. Examples of 6-membered heteroaryl groups, which can contain from 1 to 4 nitrogen atoms and/or a phosphorus atom, are 2-pyridinyl, 2-phosphabenzolyl, 3-pyridazinyl, 2-pyrimidinyl, 4-pyrimidinyl, 2-pyrazinyl, 1,3,5-triazin-2-yl and 1,2,4-triazin-3-yl, 1,2,4-triazin-5-yl and 1,2,4-triazin-6-yl. The 5-membered and 6-membered heteroaryl groups can also be substituted by $C_1$-$C_{10}$-alkyl, $C_6$-$C_{10}$-aryl, alkylaryl having from 1 to 10 carbon atoms in the alkyl part and 6-10 carbon atoms in the aryl part, trialkylsilyl or halogens such as fluorine, chlorine or bromine or be fused with one or more aromatics or heteroaromatics. Examples of benzo-fused 5-membered heteroaryl groups are 2-indolyl, 7-indolyl, 2-coumaronyl, 7-coumaronyl, 2-thianaphthenyl, 7-thianaphthenyl, 3-indazolyl, 7-indazolyl, 2-benzimidazolyl and 7-benzimidazolyl. Examples of benzo-f used 6-membered heteroaryl groups are 2-quinolyl, 8-quinolyl, 3-cinnolyl, 8-cinnolyl, 1-phthalazyl, 2-quinazolyl, 4-quinazolyl, 8-quinazolyl, 5-quinoxalyl, 4-acridyl, 1-phenanthridyl and 1-phenazyl. Nomenclature and numbering of the heterocycles has been taken from L. Fieser and M. Fieser, Lehrbuch der organischen Chemie, 3rd revised edition, Verlag Chemie, Weinheim 1957.

It is preferred that the radicals $X^D$ in the formula (XIV) are identical, preferably fluorine, chorine, bromine, $C_1$-$C_7$-alkyl or aralkyl, in particular chlorine, methyl or benzyl.

The synthesis of such complexes can be carried out by methods known per se, preferably by reaction of the appropriately substituted, cyclic hydrocarbon anions with halides of titanium, zirconium, hafnium or chromium.

Among the metallocene complexes of the formula (XIV), preference is given to (XIVa)

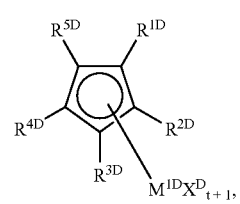

-continued

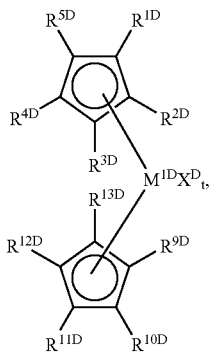
(XIVb)

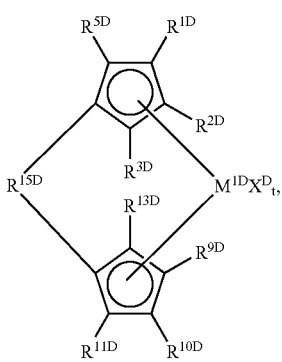
(XIVc)

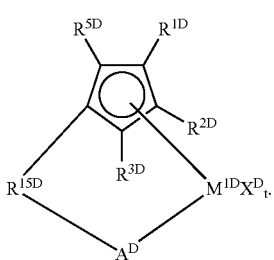
(XIVd)

Among the compounds of the formula (XIVa), particular preference is given to those in which $M^{1D}$ is titanium, vanadium or chromium, $X^D$ is chlorine, $C_1$-$C_4$-alkyl, phenyl, alkoxy or aryloxy, t is 1 or 2 and $R^{1D}$ to $R^{5D}$ are each hydrogen or $C_1$-$C_6$-alkyl or two adjacent radicals $R^{1D}$ to $R^{5D}$ form a substituted or unsubstituted benzo group.

Among the compounds of the formula (XIVb), preference is given to those in which $M^{1D}$ is titanium, zirconium, vanadium, hafnium or chromium, $X^D$ is fluorine, chlorine, $C_1$-$C_4$alkyl or benzyl, or two radicals $X^D$ form a substituted or unsubstituted butadiene ligand, t is 0 in the case of chromium, otherwise 1 or 2, preferably 2, $R^{1D}$ to $R^{5D}$ are each hydrogen, $C_1$-$C_8$-alkyl, $C_6$-$C_8$-aryl, $NR^{8D}_2$, $OSiR^{8D}_3$ or $Si(R^{8D})_3$ and $R^{9D}$ to $R^{13D}$ are each hydrogen, $C_1$-$C_8$-alkyl or $C_6$-$C_8$-aryl, $NR^{14D}_2$, $OSiR^{14D}_3$ or $Si(R^{14D})_3$ or two radicals $R^{1D}$ to $R^{5D}$ and/or $R^{9D}$ to $R^{13D}$ together with the $C_5$ ring form an indenyl or substituted indenyl system.

The compounds of the formula (XIVb) in which the cyclopentadienyl radicals are identical are particularly useful.

Examples of particularly useful compounds D) of the formula (XIVb) include: bis(cyclopentadienyl)chromium, bis (cyclopentadienyl)zirconium dichloride, bis(pentamethylcyclopentadienyl)zirconium dichloride, bis (methylcyclopentadienyl)zirconium dichloride, bis (ethylcyclopentadienyl)zirconium dichloride, bis(n-butylcyclopentadienyl)zirconium dichloride, bis(1-n-butyl-3-methylcyclopentadienyl)zirconium dichloride, bis (indenyl)zirconium dichloride, bis(tetrahydroindenyl) zirconium dichloride and bis (trimethylsilylcyclopentadienyl)zirconium dichloride and also the corresponding dimethylzirconium compounds.

Particularly useful compounds of the formula (XIVc) are those in which $R^{15D}$ is

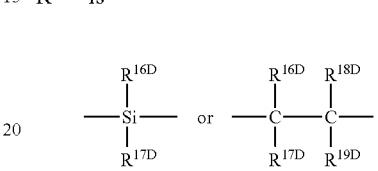

or $=BR^{16D}$ or $=BNR^{16D}R^{17D}$, $M^{1D}$ is titanium, zirconium or hafnium, in particular zirconium, and $X^D$ are identical or different and are each chlorine, $C_1$-$C_4$-alkyl, benzyl, phenyl or $C_7$-$C_{15}$-alkylaryloxy.

Especially useful compounds of the formula (XIVc) are those of the formula (XIVc')

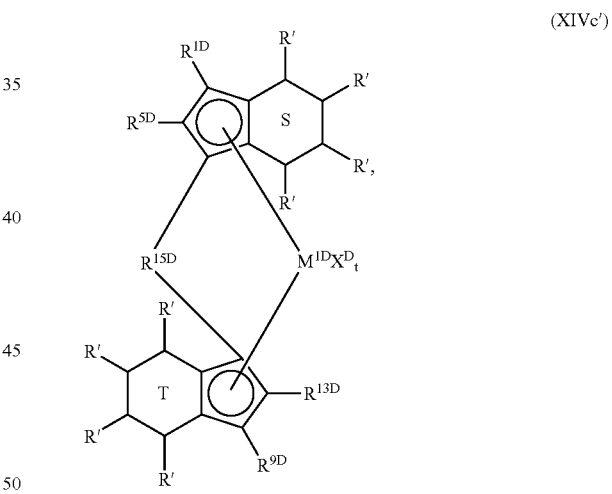
(XIVc')

where the radicals R' are identical or different and are each hydrogen, $C_1$-$C_{10}$-alkyl or $C_3$-$C_{10}$-cycloalkyl, preferably methyl, ethyl, isopropyl or cyclohexyl, $C_6$-$C_{20}$-aryl, preferably phenyl, naphthyl or mesityl, $C_7$-$C_{40}$-arylalkyl, $C_7$-$C_{40}$-alkylaryl, preferably 4-tert-butylphenyl or 3,5-di-tert-butylphenyl, or $C_8$-$C_{40}$-arylalkenyl, $R^{5D}$ and $R^{13D}$ are Identical or different and are each hydrogen, $C_1$-$C_6$-alkyl, preferably methyl, ethyl, isopropyl, n-propyl, n-butyl, n-hexyl or tert-butyl, and the rings S and T may be Identical or different and saturated, unsaturated or partially saturated.

The indenyl or tetrahydroindenyl ligands of the metallocenes of the formula (XIVc') are preferably substituted in the 2 position, the 2,4 positions, the 4,7 positions, the 2,4,7 positions, the 2,6 positions, the 2,4,6 positions, the 2,5,6 positions, the 2,4,5,6 positions or the 2,4,5,6,7 positions, in particular in the 2,4 positions, with the following numbering applying to the site of substitution:

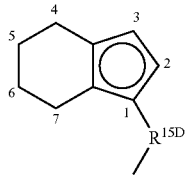

Furthermore, preference is given to using bridged bis-indenyl complexes in the rac or pseudo-rac form as component D). The term "pseudo-rac form" refers to complexes in which the two indenyl ligands are in the rac arrangement relative to one another when all other substituents of the complex are disregarded.

Further examples of particularly useful catalysts D) (XIVc) and (XIVc') include dimethylsilanediylbis(cyclopentadienyl)zirconium dichloride, dimethylsilanediylbis(indenyl)zirconium dichloride, dimethylsilanediylbis(tetrahydroindenyl)zirconium dichloride, ethylenebis(cyclopentadienyl)zirconium dichloride, ethylenebis(indenyl)zirconium dichloride, ethylenebis(tetrahydroindenyl)zirconium dichloride, tetramethylethylene-9-fluoroenylcyclopenta-dienylzirconium dichloride, dimethylsilanediylbis(3-tert-butyl-5-methylcyclopentadienyl)zirconium dichloride, dimethylsilanediylbis(3-tert-butyl-5-ethylcyclopentadienyl)zirconium dichloride, dimethylsilanediylbis(2-methylindenyl)zirconium dichloride, dimethylsilanediylbis(2-isopropylindenyl) zirconium dichloride, dimethylsilanediylbis(2-tert-butylindenyl)zirconium dichloride, diethylsilanediylbis(2-methylindenyl)zirconium dibromide, dimethylsilanediylbis(3-methyl-5-methylcyclopentadienyl)zirconium dichloride, dimethylsilanediylbis(3-ethyl-5-isopropylcyclopentadienyl) zirconium dichloride, dimethylsilanediylbis(2-ethylindenyl) zirconium dichloride, dimethylsilanediylbis(2-methyl-4,5-benzindenyl)zirconium dichloride, dimethylsilanediylbis(2-ethyl-4,5-benzindenyl)zirconium dichloride, methylphenylsilanediylbis(2-methyl-4,5-benzindenyl)zirconium dichloride, methylphenylsilanediylbis(2-ethyl-4,5-benzindenyl)zirconium dichloride, diphenylsilanediylbis(2-methyl-4,5-benzindenyl)zirconium dichloride, diphenylsilanediylbis(2-ethyl-4,5-benzindenyl)zirconium dichloride, diphenylsilanediylbis(2-methylindenyl)hafnium dichloride, dimethylsilanediylbis(2-methyl-4-phenylindenyl)zirconium dichloride, dimethylsilanediylbis(2-ethyl-4-phenylindenyl)zirconium dichloride, dimethylsilanediylbis(2-methyl-4-(1-naphthyl)indenyl)zirconium dichloride, dimethylsilanediylbis(2-ethyl-4-(1-naphthyl)indenyl)zirconium dichloride, dimethylsilanediylbis(2-propyl-4-(1-naphthyl)indenyl)zirconium dichloride, dimethylsilanediylbis(2-i-butyl-4-(1-naphthyl)indenyl)zirconium dichloride, dimethylsilanediylbis(2-propyl-4-(9-phenanthryl)indenyl) zirconium dichloride, dimethylsilanediylbis(2-methyl-4-isopropylindenyl)zirconium dichloride, dimethylsilanediylbis (2,7-dimethyl-isopropylindenyl)zirconium dichloride, dimethylsilanediylbis(2-methyl-4,6-diisopropylindenyl)zirconium dichloride, dimethylsilanediylbis(2-methyl-4[p-trifluoromethylphenyl]indenyl)zirconium dichloride, dimethylsilanediylbis(2-methyl-4-[3',5'-dimethylphenyl]indenyl) zirconium dichloride, dimethylsilanediylbis(2-methyl-4-[4'-tert-butylphenyl]indenyl)zirconium dichloride, diethylsilanediylbis(2-methyl-4-[4'-tert-butylphenyl]indenyl)zirconium dichloride, dimethylsilanediylbis(2-ethyl-4-[4'-tert-butylphenyl]indenyl)zirconium dichloride, dimethylsilanediylbis(2-propyl-4-[4'-tert-butylphenyl]indenyl) zirconium dichloride, dimethylsilanediylbis(2-isopropyl-4-[4'-tert-butylphenyl]indenyl)zirconium dichloride, dimethylsilanediylbis(2-n-butyl-4-[4'-tert-butylphenyl]indenyl)zirconium dichloride, dimethylsilanediylbis(2-hexyl-4-[4'-tert-butylphenyl]indenyl)zirconium dichloride, dimethylsilanediyl (2-isopropyl-4-phenylindenyl)(2-methyl-4-phenylindenyl)zirconium dichloride, dimethylsilanediyl(2-isopropyl-4-(1-naphthyl)indenyl)(2-methyl-4-(1-naphthyl)indenyl)zirconium dichloride, dimethylsilanediyl(2-isopropyl)-4-[4'-tert-phenyl]indenyl)(2-methyl-4-[4'-tert-butylphenyl]indenyl)zirconium dichloride, dimethylsilanediyl(2-isopropyl-4-[4'-tert-butylphenyl]indenyl)(2-ethyl-4-[4'-tert-butylphenyl]indenyl)zirconium dichloride, dimethylsilanediyl(2-isopropyl-4-[4'-tert-butylphenyl]indenyl)(2-methyl-4-[3',5'-bis-tert-butylphenyl]indenyl)zirconium dichloride, dimethylsilanediyl(2-isopropyl-4-[4'-tert-butylphenyl]indenyl)(2-methyl-4-[1'-naphthyl]indenyl)zirconium dichloride and ethylene(2-isopropyl-4-[4'-tert-butylphenyl]indenyl)(2-methyl-4-[4'-tert-butylphenyl]indenyl)zirconium dichloride, and also the corresponding dimethylzirconium, zirconium monochloride mono(alkylaryloxide) and zirconium di(alkylaryloxide) compounds. The complexes are preferably used in the rac form.

Such complexes can be synthesized by methods known per se, preferably by reaction of the appropriately substituted, cyclic hydrocarbon anions with halides of titanium, zirconium, hafnium, vanadium, niobium, tantalum or chromium. Examples of appropriate preparative methods are described, inter alia, in Journal of Organometallic Chemistry, 369 (1989), 359-370.

Particularly useful compounds of the formula (XIVd) are those in which
$M^{1D}$ is titanium or zirconium, in particular titanium, and
$X^D$ is chlorine, $C_1$-$C_4$-alkyl or phenyl or two radicals $X^D$ form a substituted or unsubstituted butadiene ligand,
$R^{15D}$ is

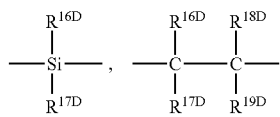

or $=BR^{16D}$ or $=BNR^{16D}R^{17D}$,
$A^{1D}$ is —O—, —S— or

t is 1 or 2, preferably 2,
$R^{1D}$ to $R^{3D}$ and $R^{5D}$ are each hydrogen, $C_1$-$C_{10}$-alkyl, preferably methyl, $C_3$-$C_{10}$-cycloalkyl, $C_6$-$C_{15}$-aryl $NR^{8D}_2$ or $Si(R^{8D})_3$, or two adjacent radicals form a cyclic group having from 4 to 12 carbon atoms, with particular preference being given to all $R^{1D}$ to $R^{3D}$ and $R^{5D}$ being methyl.

Particularly useful complexes D) of the formula (XIVd) are dimethylsilanediyl(tetramethylcyclopentadienyl)(benzylamino)titanium dichloride, dimethylsilanediyl(tetramethylcyclopentadienyl)(tert-butyl-amino)titanium dichloride, dimethylsilanediyl(tetramethylcyclopentadienyl)(adamantyl)titanium dichloride and dimethylsilanediyl(indenyl)(tert-butyl-amino)titanium dichloride.

Another group of compounds of the formula (XIVd) which are particularly useful are those in which $M^{1D}$ is titanium, vanadium or chromium, preferably in the oxidation state III, and $X^D$ is chlorine, $C_1$-$C_4$-alkyl or phenyl or two radicals $X^D$ form a substituted or unsubstituted butadiene ligand, $R^{15D}$ is

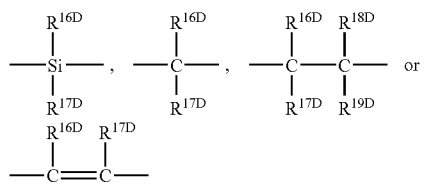

$A^{1D}$ is —O—$R^{22D}$, —$NR^{22D}{}_2$, —$PR^{22D}{}_2$ or an unsubstituted, substituted or fused, heterocyclic, in particular heteroaromatics ring system, v is 1 or when $A^{1D}$ is an unsubstituted, substituted or fused, heterocyclic ring system may be 0 or 1, and $R^{1D}$ to $R^{3D}$ and $R^{5D}$ are each hydrogen, $C_1$-$C_{10}$-alkyl, $C_3$-$C_{10}$-cycloalkyl, $C_6$-$C_{15}$-aryl or Si($R^{8D}$)$_3$, or two adjacent radicals form a cyclic group having from 4 to 12 carbon atoms.

In a preferred embodiment, $A^{1D}$ is an unsubstituted, substituted or fused, heteroaromatic ring system and $M^{1D}$ is chromium. Very particular preference is given to $A^{1D}$ being an unsubstituted or substituted, e.g. alkyl-substituted quinolyl or pyridyl, in particular one bound in position 8 or 2, and v being equal to 0, e.g. 8-quinolyl, 8-(2-methylquinolyl), 8(2,3,4-trimethylquinolyl), 8-(2,3,4,5,6,7-hexamethylquinolyl), v being 0 and $M^{1D}$ being chromium. Preferred catalysts D) of this type are 1-(8-quinolyl)-2-methyl-4-methylcyclopentadienylchromium(III) dichloride, 1-(8-quinolyl)-3-isopropyl-5-methylcyclopentadienylchromium(III) dichloride, 1-(8-quinolyl)-3-tert-butyl-5-methylcyclopentadienylchromium (III) dichloride, 1-(8-quinolyl)-2,3,4,5-tetramethylcyclopentadienylchromium(III) dichloride, 1-(8-quinolyl)tetrahydroindenylchromium(III) di-chloride, 1-(8-quinolyl)indenylchromium(III) dichloride, 1-(8-quinolyl)-2-methylindenylchromium(III) dichloride, 1-(8-quinolyl)-2-isopropylindenylchromium(III) dichloride, 1-(8-quinolyl)-2-ethylindenyl-chromium(III) dichloride, 1-(8-quinolyl)-2-tert-butylindenylchromium(III) dichloride, 1-(8-quinolyl) benzindenylchromium(III) dichloride, 1-(8-quinolyl)-2-methylbenzindenylchromium(III) dichloride, 1-(8-(2-methylquinolyl))-2-methyl-4-methylcyclopentadienylchromium(III) dichloride, 1-(8-(2-methylquinolyl))-2,3,4,5-tetramethylcyclopentadienylchromium(III) dichloride, 1-(8-(2-methylquinolyl))tetrahydroindenylchromium(III) dichloride, 1-(8-(2-methylquinolyl))indenyl-chromium(III) dichloride, 1-(8-(2-methylquinolyl))-2-methylindenylchromium(III) dichloride, 1-(8-(2-methylquinolyl))-2-isopropylindenylchromium(III) dichloride, 1-(8-(2-methylquinolyl))-2-ethylindenylchromium(III) dichloride, 1-(8-(2-methylquinolyl))-2-tert-butylindenylchromium(III) di-chloride, 1-(8-(2-methylquinolyl))benzindenylchromium (III) dichloride 1-(2-pyridylethyl)indenyl-chromium (III) dichloride or 1-(8-(2-methylquinolyl))-2-methylbenzindenylchromium(III) dichloride.

Furthermore, owing to the ease of preparation, preference is given to compounds in which $R^{15D}$ is CH=CH or 1,2-phenylene and $A^{1D}$ is $NR^{22D}{}_2$, and compounds in which $R^{15D}$ is $CH_2$, $C(CH_3)_2$ or $Si(CH_3)_2$ and $A^{1D}$ is unsubstituted or substituted 2- or 8-quinolyl or unsubstituted or substituted 2-pyridyl.

The preparation of such functional cyclopentadienyl ligands has been known for a long time. Various synthetic routes to these complexing ligands are described, for example, by M. Enders et al. in Chem. Ber. (1996), 129, 459-463, or P. Jutzi and U. Siemeling in J. Orgmet. Chem. (1995), 500, 175-185.

The metal complexes, in particular the chromium complexes, can be obtained in a simple manner by reacting the appropriate metal salts, e.g. metal chlorides, with the ligand anion (e.g. using methods analogous to the examples in DE-A-19710615).

Further suitable catalysts D) include metallocenes having at least one ligand which is formed from a cyclopentadienyl or heterocyclopentadienyl and a fused-on heterocycle, with the heterocycles preferably being aromatic and containing nitrogen and/or sulfur. Such compounds are described, for example, in WO 98/22486. These are in particular dimethylsilanediyl(2-methyl-4-phenyl-indenyl)(2,5-dimethyl-N-phenyl-4-azapentalene)zirconium dichloride, dimethylsilanediylbis(2-methyl-4-phenyl-4-hydroazulenyl)zirconium dichloride, dimethylsilanediylbis(2-ethyl-4-phenyl-4-hydroazulenyl)zirconium dichloride, bis(2,5-dimethyl-N-phenyl-4-azapentalene)zirconium dichloride or (indenyl)(2,5-dimethyl-N-phenyl-4-azapentalene)zirconium dichloride.

Further suitable catalysts D) are systems in which a metallocene compound is combined with, for example, an inorganic oxide which has been treated with zirconium alkoxide and subsequently chlorinated, for example by means of carbon tetrachloride. The preparation of such systems is described, for example, in WO 01/41920.

Other suitable catalysts D) include imidochromium compounds in which chromium bears at least one imido group as structural feature. These compounds and their preparation are described, for example, in WO 01/09148.

Further suitable components D) include transition metal complexes with a tridentate macrocyclic ligand, in particular substituted and unsubstituted 1,3,5-triazacyclohexanes and 1,4,7-triazacyclononanes. In the case of this type of catalyst, preference is likewise given to chromium complexes. Preferred catalysts of this type are [1,3,5tri(methyl)-1,3,5-triazacyclohexane]chromium trichloride, [1,3,5-tri(ethyl)-1,3,5-triazacyclohexane]chromium trichloride, [1,3,5tri(octyl)-1,3,5-triazacyclohexane]chromium trichloride, [1,3,5tri(dodecyl)-1,3,5-triazacyclohexane]chromium trichloride and [1,3,5tri(benzyl)-1,3,5-triazacyclohexane]chromium trichloride.

Further suitable catalysts D) are, for example, transition metal complexes with at least one ligand of the formulae XV to XIX,

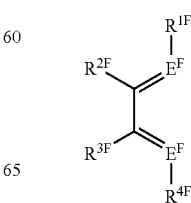

XV

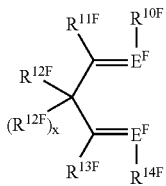

XVI

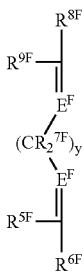

XVII

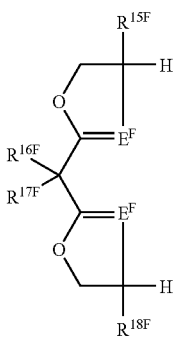

XVIII

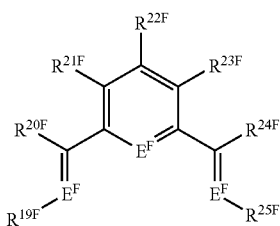

XIX where the transition metal is selected from among the elements Ti, Zr, Hf, Sc, V, Nb, Ta, Cr, Mo, W, Fe, Co, Ni, Pd, Pt and the elements of the rare earth metals. Preference is given to compounds having nickel, iron, cobalt or palladium as central metal.

$E^F$ is an element of group 15 of the Periodic Table of the Elements, preferably N or P, with particular preference being given to N. The two or three atoms $E^F$ in a molecule can be identical or different.

The radicals $R^{1F}$ to $R^{25F}$, which may be identical or different within a ligand system XV to XIX, are as follows:

$R^{1F}$ and $R^{4F}$ are each, independently of one another, a hydrocarbon radical or a substituted hydrocarbon radical, preferably a hydrocarbon radical in which the carbon atom adjacent to the element $E^F$ is bound to at least two carbon atoms, $R^{2F}$ and $R^{3F}$ are each, independently of one another, hydrogen, a hydrocarbon radical or a substituted hydrocarbon radical, where $R^{2F}$ and $R^{3F}$ together may also form a ring system in which one or more heteroatoms may be present, $R^{6F}$ and $R^{8F}$ are each, independently of one another, a hydrocarbon radical or substituted hydrocarbon radical, $R^{5F}$ and $R^{9F}$ are each, independently of one another, hydrogen, a hydrocarbon radical or a substituted hydrocarbon radical, where $R^{6F}$ and $R^{5F}$ or $R^{8F}$ and $R^{9F}$ may together also form a ring system, $R^{7F}$ are each, independently of one another, hydrogen, a hydrocarbon radical or a substituted hydrocarbon radical, where two $R^{7F}$ may together also form a ring system, $R^{10F}$ and $R^{14F}$ are, independently of one another, a hydrocarbon radical or a substituted hydrocarbon radical, $R^{11F}$, $R^{12F}$, $R^{12F'}$ and $R^{13F}$ are each, independently of one another, hydrogen, a hydrocarbon radical or a substituted hydrocarbon radical, where two or more geminal or vicinal radicals $R^{11A}$, $R^{12A}$, $R^{12A'}$ and $R^{13A}$ may together form a ring system, $R^{15F}$ and $R^{18F}$ are each, independently of one another, hydrogen, a hydrocarbon radical or a substituted hydrocarbon radical, $R^{16F}$ and $R^{17F}$ are each, independently of one another, hydrogen, a hydrocarbon radical or a substituted hydrocarbon radical, $R^{19F}$ and $R^{25F}$ are each, independently of one another, $C_2$-$C_{20}$-alkenyl, $C_6$-$C_{20}$-aryl, alkylaryl having from 1 to 10 carbon atoms in the alkyl part and 6-20 carbon atoms in the aryl part, where the organic radicals $R^{19F}$ and $R^{25F}$ may also be substituted by halogens, $R^{20F}$-$R^{24F}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{26F}_3$, where the organic radicals $R^{20F}$-$R^{24F}$ may also be substituted by halogens and two vicinal radicals $R^{20F}$-$R^{24F}$ may also be joined to form a five- or six-membered ring and $R^{26F}$ are each, independently of one another, hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl part and 6-20 carbon atoms in the aryl part and two radicals $R^{26F}$ may also be joined to form a five- or six-membered ring.

x is 0 or 1, with the complex of the formula (XVI) being negatively charged when x=0, and y is an integer from 1 to 4, preferably 2 or 3.

Particularly useful transition metal complexes are those having Fe, Co, Ni, Pd or Pt as central metal and containing ligands of the formula (XV). Particular preference is given to diimine complexes of Ni or Pd, e.g.:

Di(2,6-diisopropylphenyl)-2,3-dimethyldiazabutadienepalladium dichloride, di(diisopropylphenyl)-2,3-dimethyldiazabutadienenickel dichloride, di(2,6-diisopropyl-phenyl) dimethyldiazabutadienedimethylpalladium, di(2,6-diisopropylphenyl)-2,3-dimethyldiazabutadienedimethylnickel, di(2,6-dimethylphenyl)-2,3-dimethyldiazabutadienepalladium dichloride, di(2,6-dimethylphenyl)-2,3-dimethyldiazabutadienenickel dichloride, di(2,6-dimethylphenyl)-2,3-dimethyldiazabutadienedimethylpalladium, di(2,6-dimethylphenyl)-2,3-dimethyldiazabutadienedimethylnickel, di(2-methylphenyl)-2,3-dimethyldiazabutadienepalladium dichloride, di(2-methylphenyl)-2,3-dimethyldiazabutadienenickel dichloride, di(2-methylphenyl)-2,3-dimethyldiazabutadienedimethylpalladium, di(2-methylphenyl)-2,3-dimethyldiazabutadienedimethylnickel, diphenyl-2,3-dimethyldiazabutadienepalladium dichloride, diphenyl-2,3-dimethyldiazabutadienenickel dichloride, diphenyl-2,3-dimethyldiazabutadienedimethylpalladium, diphenyl-2,3-dimethyldiazabutadienedimethylnickel, di(2,6-dimethylphenyl)azanaphthenepalladium dichloride, di(2,6- dimethylphenyl)azanaphthenenickel dichloride, di(2,6-dimethylphenyl)azanaphthenedimethylpalladium, di(2,6-dimethyl-phenyl)azanaphthenedimethylnickel, 1,1'-bipyridylpalladium dichloride, 1,1'-bipyridylnickel dichloride, 1,1'-bipyridyl(dimethyl)palladium, 1,1'-bipyridyl (dimethyl)nickel.

Particularly useful compounds (XIX) also include those which are described in J. Am. Chem. Soc. 120, p. 4049 ff. (1998), J. Chem. Soc., Commun. 1998, 849, and WO 98/27124. $E^F$ is preferably nitrogen and $R^{19F}$ and $R^{25F}$ in (XIX) are preferably phenyl, naphthyl, biphenyl, anthranyl, o-, m-, p-methylphenyl, 2,3-, 2,4-, 2,5- or 2,6-dimethylphenyl, -dichlorophenyl or -dibromophenyl, 2-chloro-6-methylphenyl, 2,3,4-, 2,3,5-, 2,3,6-, 2,4,5-, 2,4,6- or 3,4,5-trimethylphenyl, in particular 2,3- or 2,6-dimethylphenyl, -diisopropylphenyl, -dichlorophenyl or -dibromophenyl and 2,4,6-trimethylphenyl. At the same time, $R^{20F}$ and $R^{24F}$ are preferably hydrogen, methyl, ethyl, n-propyl, isopropyl, n-butyl, tert-butyl, n-pentyl, n-hexyl, n-heptyl, n-octyl, benzyl or phenyl, in particular hydrogen or methyl. $R^{21F}$ and $R^{23F}$ are preferably hydrogen and $R^{22F}$ is preferably hydrogen, methyl, ethyl or phenyl, in particular hydrogen. Preference is given to complexes of the ligands XIX with the transition metals Fe, Co or Ni, in particular Fe. Particular preference is given to 2,6-diacetylpyridinebis(2,4-dimethylphenylimine) iron dichloride, 2,6-diacetylpyridinebis(2,4,6-trimethylphenylimine)iron dichloride, 2,6-diacetylpyridinebis(2-chloro-6-methylphenylimine)iron dichloride, 2,6-diacetylpyridinebis(2,6-diisopropylphenylimine)iron dichloride, 2,6-diacetylpyridinebis(2,6-dichlorophenylimine)iron dichloride, 2,6-pyridinedicarboxaldehydebis (2,6-diisopropylphenylimine)iron dichloride, 2,6-diacetylpyridinebis(2,4-dimethylphenylimine)cobalt dichloride, 2,6-diacetylpyridinebis(2,4,6-trimethylphenylimine)cobalt dichloride, 2,6-diacetylpyridinebis(2-chloro-6-methylphenylimine)cobalt dichloride, 2,6-diacetylpyridinebis(2,6-diisopropylphenylimine)cobalt dichloride, 2,6-diacetylpyridinebis(2,6-dichlorophenylimine)cobalt dichloride, and 2,6-pyridinedicarboxaldehydebis(2,6-diisopropylphenylimine)cobalt dichloride.

Iminophenoxide complexes can also be used as catalysts D). The ligands of these complexes can be prepared, for example, from substituted or unsubstituted salicylaldehydes and primary amines, in particular substituted or unsubstituted arylamines. Transition metal complexes with pi ligands having one or more heteroatoms in the pi system, for example the boratabenzene ligand, the pyrrolyl anion or the phospholyl anion, can also be used as catalysts D).

Further complexes suitable as catalysts D) include those which have bidentate or tridentate chelating ligands. In such ligands, for example, an ether function is linked to an amine or amide function or an amide is linked to a heteroaromatic such as pyridine.

Such combinations of components A) and D) enable, for example, bimodal products to be prepared or comonomers to be generated in situ. Preference is given to using at least one transition metal complex A) in the presence of at least one further catalyst D) customary for the polymerization of olefins and if desired, one or more activating compounds C). Here, depending the catalyst combinations A) and D), one or more activating compounds C) may be advantageous. The polymerization catalysts D) can likewise be supported and can be used simultaneously or in any order with the complex A) of the present invention. For example, the transition metal complex A) and the polymerization catalysts D) can be applied together to a support B) or different supports B). It is also possible to use mixtures of various catalysts as component D). The molar ratio of transition metal complex A) to polymerization catalyst D) is usually in the range from 1:100 to 100:1, preferably from 1:10 to 20:1 and particularly preferably from 1:1 to 10:1.

The catalyst system may further comprise, as additional component E), a metal compound of the formula (XX), $$M^G(R^{1G})_{r^G}(R^{2G})_{s^G}(R^{3G})_{t^G} \qquad (XX)$$

where $M^G$ is U, Na, K, Be, Mg, Ca, Sr, Ba, boron, aluminum, gallium, indium, thallium, zinc, in particular U, Na, K, Mg, boron, aluminum or Zn, $R^{1G}$ is hydrogen, $C_1$-$C_{10}$-alkyl, $C_6$-$C_{15}$-aryl, alkylaryl or arylalkyl each having from 1 to 10 carbon atoms in the alkyl part and from 6 to 20 carbon atoms in the aryl part, $R^{2G}$ and $R^{3G}$ are each hydrogen, halogen, $C_1$-$C_{10}$-alkyl, $C_6$-$C_{15}$-aryl, alkylaryl, arylalkyl or alkoxy each having from 1 to 20 carbon atoms in the alkyl radical and from 6 to 20 carbon atoms in the aryl radical, or alkoxy with $C_1$-$C_{10}$-alkyl or $C_6$-$C_{15}$-aryl, $r^G$ is an integer from 1 to 3 and $s^G$ and $t^G$ are integers from 0 to 2, with the sum $r^G+s^G+t^G$ corresponding to the valence of $M^G$, where the component E) is not identical to the component C). It is also possible to use mixtures of various metal compounds of the formula (XX).

Among the metal compounds of the formula (XX), preference is given to those in which $M^G$ is lithium, magnesium, boron or aluminum and $R^{1G}$ is $C_1$-$C_{20}$-alkyl.

Particularly preferred metal compounds of the formula (XX) are methyllithium, ethyllithium, n-butyllithium, methylmagnesium chloride, methylmagnesium bromide, ethylmagnesium chloride, ethylmagnesium bromide, butylmagnesium chloride, dimethylmagnesium, diethylmagnesium, dibutylmagnesium, n-butyl-n-octylmagnesium, n-butyl-n-heptylmagnesium, in particular n-butyl-n-octylmagnesium, tri-n-hexylaluminum, triisobutylaluminum, tri-n-butylaluminum, triethylaluminum, dimethylaluminum chloride, dimethylaluminum fluoride, methylaluminum dichloride, methylaluminum sesquichloride, diethylaluminum chloride and trimethylaluminum and mixtures thereof. The partial hydrolysis products of aluminum alkyls with alcohols can also be used.

When a metal compound E) is used, it is preferably present in the catalyst system in such an amount that the molar ratio of $M^G$ from formula (XX) to transition metal from transition metal compound A) is from 2000:1 to 0.1:1, preferably from 800:1 to 0.2:1 and particularly preferably from 100:1 to 1:1.

In general, the catalyst solid together with the further metal compound E) of the formula (XX), which may be different from the metal compound or compounds E) used in the preparation of the catalyst solid, is used as constituent of a catalyst system for the polymerization or copolymerization of olefins. It is also possible, particularly when the catalyst solid does not contain any activating component C), for the catalyst system to further comprise, in addition to the catalyst solid, one or more activating compounds C) which are identical to or different from any activating compounds C) present in the catalyst solid.

To prepare the catalyst systems of the present invention, preference is given to immobilizing at least one of the components A) and/or C) on the support B) by physisorption or by means of chemical reaction, i.e. covalent binding of the components, with reactive groups of the support surface. The order in which the support component B), the component A) and any component C) are combined is immaterial. The components A) and C) can be added independently of one another or simultaneously or in premixed form to B). After the individual process steps, the solid can be washed with suitable inert solvents such as aliphatic or aromatic hydrocarbons.

In a preferred embodiment the transition metal complex A) is brought into contact with the activating compound C) in a suitable solvent, usually giving a soluble reaction product, an adduct or a mixture. The preparation obtained in this way is then brought into contact with the support B), which may have been pretreated, and the solvent is completely or partly removed. This preferably gives a solid in the form of a free-flowing powder. Examples of the industrial implementation of the above process are described in WO 96/00243, WO 98/40419 or WO 00/05277. A further preferred embodiment comprises firstly applying the activating compound C) to the support B) and subsequently bringing this supported activating compound into contact with the transition metal complex A).

The component D) can likewise be reacted in any order with the components A) and, if desired, B), C) and E). Preference is given to bringing D) firstly into contact with component C) and then dealing with the components A) and B) and any further C) as described above. In another preferred embodiment, a catalyst solid is prepared from the components A), B) and C) as described above and this is brought into contact with the component E) during, at the beginning of or shortly before the polymerization. Preference is given to E) firstly being brought into contact with the α-olefin to be polymerized and the catalyst solid comprising the components A), B) and C) as described above subsequently being added. The transition metal complex A) can be brought into contact with the component(s) C) and/or D) either before or after being brought into contact with the olefin to be polymerized. Preactivation using one or more components C) prior to mixing with the olefin and further addition of the same or different components C) and/or D) after this mixture has been brought into contact with the olefin is also possible. Preactivation is generally carried out at 10-100° C., in particular 20-80° C.

It is also possible for the catalyst system firstly to be prepolymerized with α-olefins, preferably linear $C_2$-$C_{10}$-1-alkenes and in particular ethylene or propylene, and the resulting prepolymerized catalyst solid then to be used in the actual polymerization. The mass ratio of catalyst solid used in the prepolymerization to monomer polymerized onto it is usually in the range from 1:0.1 to 1:1000, preferably from 1:1 to 1:200.

Furthermore, a small amount of an olefin, preferably an α-olefin, for example vinylcyclohexane, styrene or phenyldimethylvinylsilane, as modifying component, an antistatic or a suitable inert compound such as a wax or oil can be added as additive during or after the preparation of the catalyst system. The molar ratio of additives to transition metal compound B) is usually from 1:1000 to 1000:1, preferably from 1:5 to 20:1.

The catalyst systems of the present invention are suitable for the polymerization of olefins and especially for the polymerization of α-olefins, i.e. hydrocarbons having terminal double bonds. Suitable monomers also include functionalized olefinically unsaturated compounds such as acrolein, ester or amide derivatives of acrylic or methacrylic acid, for example acrylates, methacrylates or acrylonitrile, or vinyl esters, for example vinyl acetate. Preference is given to nonpolar olefinic compounds, including aryl-substituted α-olefins. Particularly preferred α-olefins are linear or branched $C_2$-$C_{12}$-1-alkenes, in particular linear $C_2$-$C_{10}$-1-alkenes such as ethene, propene, 1-butene, 1-pentene, 1-hexene, 1-heptene, 1-octene, 1-decene or branched $C_2$-$C_{10}$-1-alkenes such as 4-methyl-1-pentene, conjugated and unconjugated dienes such as 1,3-butadiene, 1,5-hexadiene or 1,7-octadiene or vinylaromatic compounds such as styrene or substituted styrene. It is also possible to polymerize mixtures of various α-olefins. Preference is given to polymerizing at least one olefin selected from the group consisting of ethene, propene, 1-butene, 1-pentene, 1-hexene, 1-heptene, 1-octene and 1-decene.

Suitable olefins also include ones in which the double bond is part of a cyclic structure which can have one or more ring systems. Examples are cyclopentene, cyclohexene, norbornene, tetracyclododecene and methylnorbornene and dienes such as 5-ethylidine-2-norbornene, norbornadiene or ethylnorbornadiene.

Mixtures of two or more olefins can also be polymerized. In contrast to some known iron and cobalt complexes, the transition metal complexes of the present invention display a good polymerization activity even in the case of higher α-olefins, so that their suitability for copolymerization deserves particular emphasis, in particular, the transition metal complexes of the present invention can be used for the polymerization or copolymerization of ethene or propene. As comonomers in the polymerization of ethene, preference is given to using $C_3$-$C_8$-α-olefins or norbornene, in particular 1-butene, 1-pentene, 1-hexene and/or 1-octene. Preference is given to using monomer mixtures containing at least 50 mol % of ethene. Preferred comonomers in the polymerization of propylene are ethene and/or butene.

The polymerization can be carried out in a known manner in bulk, in suspension, in the gas phase or in a supercritical medium in the customary reactors used for the polymerization of olefins. It can be carried out batchwise or preferably continuously in one or more stages. High-pressure polymerization processes in tube reactors or autoclaves, solution processes, suspension processes, stirred gas-phase processes or gas-phase fluidized-bed processes are all possible.

The polymerizations are usually carried out at from −60 to 350° C. under pressures of from 0.5 to 4000 bar at mean residence times of from 0.5 to 5 hours, preferably from 0.5 to 3 hours. The advantageous pressure and temperature ranges for carrying out the polymerizations usually depend on the polymerization method. In the case of high-pressure polymerization processes, which are usually carried out at pressures of from 1000 to 4000 bar, in particular from 2000 to 3500 bar, high polymerization temperatures are generally also set. Advantageous temperature ranges for these high-pressure polymerization processes are from 200 to 320° C., in particular from 220 to 290° C. In the case of low-pressure polymerization processes, a temperature which is at least a few degrees below the softening temperature of the polymer is generally set. These polymerization processes are preferably carried out at from 50 to 180° C., preferably from 70 to 120° C. In the case of suspension polymerization, the polymerization is usually carried out in a suspension medium, preferably an inert hydrocarbon such as isobutane or a mixture of hydrocarbons, or else in the monomers themselves. The polymerization temperatures are generally in the range from −20 to 115° C., and the pressure is generally in the range from 1 to 100 bar. The solids content of the suspension is generally in the range from 10 to 80%. The polymerization can be carried out batchwise, e.g. in stirring autoclaves, or continuously, e.g. in tube reactors, preferably in loop reactors. Particular preference is given to employing the Phillips PF process as described in U.S. Pat. No. 3,242,150 and U.S. Pat. No. 3,248,179. The gas-phase polymerization is generally carried out at from 30 to 125° C.

Among the abovementioned polymerization processes, particular preference is given to gas-phase polymerization, in particular in gas-phase fluidized-bed reactors, solution polymerization and suspension polymerization, in particular in loop reactors and stirred tank reactors. The gas-phase polymerization can also be carried out in the condensed or supercondensed phase, in which part of the circulating gas is cooled to below the dew point and is recirculated as a two-phase mixture to the reactor. It is also possible to use a multizone reactor in which two polymerization zones are linked to one another and the polymer is passed alternately through these two zones a number of times. The two zones can also have different polymerization conditions. Such a reactor is described, for example, in WO 97/04015. The different or identical polymerization processes can also, if desired, be connected in series so as to form a polymerization cascade, for example in the Hostalen process. A parallel reactor arrangement using two or more identical or different processes is also possible. Furthermore, molar mass regulators, for example hydrogen, or customary additives such as antistatics can also be used in the polymerizations.

The transition metal complexes of the present invention and the catalyst systems in which they are present can also be prepared by means of combinations of methods or their polymerization activity can be tested with the aid of these combined methods.

The process of the present invention allows polymers of olefins to be prepared. The term "polymerization" as used here in the description of the present invention encompasses both polymerization and oligomerization, i.e. oligomers and polymers having molar masses $M_w$ in the range from about 56 to 10000000 can be produced by this process.

Owing to their good mechanical properties, the olefin polymers prepared using the catalyst system of the present invention are particularly useful for the production of films, fibers and moldings.

The catalyst systems of the present invention give polymers having very high molar masses. In addition, the catalyst systems of the present invention display a good activity even at a relatively low molar ratio of aluminoxane to organic transition metal compound.

EXAMPLES

All syntheses and polymerizations were carried out in a protective nitrogen atmosphere.

The density [g/cm$^3$] was determined in accordance with ISO 1183.

The determination of the molar mass distributions and the means $M_n$, $M_w$ and $M_w/M_n$ derived therefrom was carried out by means of high-temperature gel permeation chromatography using a method based on DIN 55672 under the following conditions: solvent: 1,2,4-trichlorobenzene, flow: 1 ml/min, temperature: 140° C., calibration using PE standards.

The DSC melting point was determined in accordance with ISO 3146.

The Staudinger index (η)[dl/g] was determined on an automatic Ubbelohde viscometer (Lauda PVS 1) using decalin as solvent at 130° C. (ISO1628 at 130° C., 0.001 g/ml of decalin).

The number of methyl side chains per 1000 carbon atoms of the polymer chain (CH$_3$/1000) was determined by means of IR.

The NMR spectra were measured on a Bruker DRX 200 ($^1$H: 200.13 MHz; $^{31}$P: 81.01 MHz) or Bruker AC 300 ($^1$H: 300.13 MHz; $^{31}$P: 121.49 MHz). The signal of the incompletely deuterated part of the solvent used served as internal standard for the $^1$H-NMR spectra. 30% $H_3PO_4$ in $D_2O$ served as external standard for measuring the $^{31}$P-NMR spectra. All signals were calibrated to the corresponding literature values.

Mass spectra were recorded on a Finnigan MAT 8230 instrument, and high resolution mass spectra were measured on a Micromass CTD ZAB-2F VH spectrometer.

Coupled GC/MS mass spectra were recorded using an HP 5890 II gas chromatograph (column HP-5, methylsilicone with 5% of phenylsilicone, 30 m×0.25 mm×0.25 µm) with HP 5971 MSD.

The starting Imidazole compounds are commercially available (Aldrich) and the dialkoxy-protected derivatives were prepared as described by N. J. Curtis, R. S. Brown, J. Org. Chem. 1980, 45, 4038.

Abbreviations used in the table below:
Cat. Catalyst
t(poly) Polymerization time
Polymer Amount of polymer formed
$M_w$ Weight average molar mass
$M_n$ Number average molar mass
Density Polymer density
Prod. Productivity of the catalyst in g of polymer obtained per mmol of catalyst (transition metal complex) used per hour
DSC Melting point determined by DSC

Example 1

1.1. Preparation of tris(1-benzylimidazol-2-yl)phosphine

A solution of 3.16 g (20 mmol) of 1-benzylimidazole in 250 ml of diethyl ether was cooled to −50° C. and 8 ml of n-BuLi solution (2.5 M in hexane, 20 mmol) were added dropwise. After stirring at −50° C. for 1 hour, the mixture was warmed to room temperature over a period of one hour. The solution was subsequently cooled to −78° C. and a solution of 0.91 g (6.6 mmol) of phosphorus trichloride in 8 ml of diethyl ether was slowly added dropwise. After the addition was complete, the resulting suspension was stirred at −78° C. for another 2 hours, brought to room temperature and then stirred for a further 14 hours at room temperature. The reaction mixture obtained in this way was filtered and the pulverulent residue was washed with a number of portions of cold diethyl ether, dried in a high vacuum and recrystallized from ethanol. The solid obtained was suspended in 100 ml of dichloromethane and stirred with 50 ml of concentrated ammonia for 1 hour. The organic phase was filtered through a thin layer of silica gel, which was then washed with a number of portions of dichloromethane. The solvent was distilled off and the solid was dried in a high vacuum. This gave 1.6 g (3.2 mmol) (48%) of tris(1-benzylimidazol-2-yl)phosphine.

MS (EI): m/e (%)=502 (100) [M]$^+$, 411 (11) [M-benzyl]$^+$, 344 (14) [M-benzylimidazole]$^+$, 247 (55) [M-benzylimidazole-imidazole-P]$^+$, 187 (26) [M-2-benzylimidazole]$^+$, 91 (66) [benzyl]$^+$.

$^1$H-NMR (300 MHz, CDCl$_3$): δ=5.18 (s, 6 H, H$^6$), 6.87 (m, 9 H, 3 H$^4$, 6 H$^8$), 7.15 (m, 12 H, 6 H$^9$+3 H$^{10}$+3 H$^5$).

$^{31}$P-NMR (121.5 MHz, CDCl$_3$): δ=−64.7.

1.2. Preparation of trichlorotris(1-benzylimidazol-2-yl)phosphinetitanium(III)

A solution of 0.06 g (0.4 mmol) of titanium(III) trichloride in 20 ml of dichloromethane was slowly added at room temperature to a solution of 0.3 g (0.6 mmol) of tris(1-benzylimidazol-2-yl)phosphine in 5 ml of dichloromethane while stirring. The solution obtained in this way was stirred at room temperature for 12 hours, resulting in formation of an olive green precipitate which was filtered off, subsequently washed with hexane and dried in a high vacuum. This gave 0.24 g (90%) of trichlorotris(1-benzylimidazol-2-yl)phosphinetitanium(III) as an olive green solid.

MS (FAB): m/e (%)=772 (100), 620 (18) [M−Cl]+, 601 (38), 503 (20) [M−TiCl$_3$+H]+.

MS (HR-FAB): $C_{30}H_{27}N_6PTi^{35}Cl_2$ calc.: 620.0891 found: 620.0873

Example 2

2.1. Preparation of tris(1-ethylhexylimidazol-2-yl)phosphine

A solution of 10 mmol of ethylhexylimidazole in 100 ml of diethyl ether was cooled to −40° C. and 4 ml of n-BuLi solution (2.5 M in hexane, 10 mmol) were added dropwise. After stirring at −40° C. for 1 hour, the solution was cooled to −78° C. and a solution of 3.33 mmol of phosphorus trichloride in 10 ml of diethyl ether was slowly added dropwise. After the addition was complete, the resulting suspension was stirred at −78° C. for another 2 hours, brought to room temperature and then stirred for a further 14 hours at room temperature. The reaction mixture obtained in this way was filtered and the pulverulent residue was washed with a number of portions of cold diethyl ether, dried in a high vacuum and recrystallized from ethanol. The solid obtained in this way was suspended in 100 ml of dichloromethane and stirred with 50 ml of concentrated ammonia for 1 hour. The organic phase was filtered through a thin layer of silica gel which was then washed with a number of portions of dichloromethane. The solid was distilled off and the solid was dried in a high vacuum. This gave tris(1-ethylhexylimidazol-2-yl)phosphine in a yield of 12%.

$^1$H-NMR (300 MHz, CDCl$_3$): δ=0.76 (m, 6H, CH$_3$), 1.10 (m, 8H, CH$_2$), 1.50 (m, 1H, H$^7$), 3.88 (d, J=7.3 Hz, 2H, N—CH$_2$), 7.02 (1H, H$^{4(5)}$), 7.15 (1H, H$^{4(5)}$).

$^{31}$P-NMR (121.5 MHz, CDCl$_3$): δ=−61.6.

MS (FAB): m/e (%)=568 (100), 539 (11), 511 (11), 390 (15), 291 (11), 179 (29), 161 (13), 150 (12), 113 (12).

2.2. Preparation of trichlorotris(1-ethylhexylimidazol-2-yl)phosphinetitanium(III)

25 ml of dichloromethane were added at room temperature to a mixture of 0.158 g (1.02 mmol) of titanium(III) trichloride and 0.682 g (1.2 mmol) of tris(1-ethylhexylimidazol-2-yl)phosphine. The reaction mixture was stirred at room temperature for 12 hours, filtered, the resulting solution was evaporated to a volume of 1 ml and subsequently admixed with hexane. This resulted in formation of an olive green precipitate which was filtered off, subsequently washed with a mixture of tetrahydrofuran and hexane and dried in a high vacuum. This gave 0.72 g (0.99 mmol, 97%) of trichlorotris (1-ethylhexylimidazol-2-yl)phosphinetitanium(III) as an olive green solid.

MS (FAB): m/e (%)=723 (63) [M]+, 686 (100) [M−Cl$_2$]+, 667 (67).

MS (HR-FAB): $C_{33}H_{57}N_6PTi^{35}Cl_2$ calc. 686.3239 found: 686.3231

Example 3

Preparation of trichlorotris(1-benzylimidazol-2-yl) phosphinevanadium(III)

A solution of 0.11 g (0.3 mmol) of vanadium(III) trichloride-tris(tetrahydrofuran) in 5 ml of dichloromethane was added slowly at room temperature to a solution of 0.19 g (0.38 mmol) of tris(1-benzylimidazol-2-yl)phosphine (Example 1.1.) in 5 ml of dichloromethane while stirring. The solution obtained in this way was stirred at room temperature for 4 hours, the dichloromethane was distilled off and the residue was washed with tetrahydrofuran and dried in a high vacuum. This gave 0.16 g (0.24 mmol, 80%) of trichlorotris(1-benzylimidazol-2-yl)phosphinevanadium(III) as a violet solid.

MS (FAB): 623 (28) [M−Cl]+, 604 (50) [M−2Cl+O]+, 588 (6) [M−2Cl]+, 503 (14) (PBzlm$_3$+H).

MS (HR-FAB): $C_{30}H_{27}N_6PV^{35}Cl_2$ calc.: 623.0851 found: 623.0812  $C_{30}H_{27}N_6PV^{37}Cl^{35}Cl$ calc.: 625.0822 found: 625.0819

Example 4

Preparation of trichlorotris(1-benzylimidazol-2-yl) phosphinechromium(III)

A solution of 0.31 g (0.62 mmol) of tris(1-benzylimidazol-2-yl)phosphine (cf. Example 1.1.) in 1.5 ml of dichloromethane was slowly added at room temperature to a solution of 0.18 g (0.48 mmol) of chromium(III) trichloride-tris(tetrahydrofuran) in 25 ml of dichloromethane while stirring. The solution obtained in this way was stirred at room temperature for 14 hours, the dichloromethane was distilled off, the residue was washed with tetrahydrofuran and dried in a high vacuum. This gave 0.25 g (0.38 mmol, 79%) of trichlorotris(1-benzylimidazol-2-yl)phosphinechromium(III) as a green solid.

$^1$H-NMR (200 MHz, CD$_2$Cl$_2$): δ=1.25 (d, J (P,H)=6.7 Hz, 6H, CH2), 2.01 (s(br), 3H, H4), 4.09 (d, J (P,H)=5.7 Hz, 3H, H5), 6.7-8.4 (s(br), 15H, H-aryl).

$^{31}$P-NMR (81.01 MHz, CD$_2$Cl$_2$): δ=6.1.

MS (FAB): m/e (%)=624 (100) [M−Cl]+, 589 (37) [M−2Cl]+, 498 (12) [M−2Cl-benzyl]+.

Example 5

Preparation of trichlorotris(1-ethylhexylimidazol-2-yl)phosphinechromium(III)

10 ml of tetrahydrofuran were added at room temperature to a mixture of 0.038 g (0.1 mmol) of chromium(III) trichloride-tris(tetrahydrofuran) and 0.2 g (0.35 mmol) of tris(1-ethylhexylimidazol-2-yl)phosphine (cf. Example 2.1.). The reaction mixture was stirred at room temperature for 12 hours, filtered, the resulting solution was evaporated to a volume of 1 ml and subsequently admixed with 5 ml of hexane. This resulted information of a light-green precipitate which was filtered off, subsequently washed with hexane and dried in a high vacuum. This gave 0.069 g (95%) of trichlorotris(1-ethylhexylimidazol-2-yl)phosphinechromium(III) as a green solid.

MS (FAB): m/e (%)=779 (23) [M+Na]+, 690 (44) [M−Cl]+, 655 (28) [M−2Cl]+, 591 (44), 569 (100), 390 (40), 179 (50), 165 (30).

MS (HR-FAB): calc. 690.3164 found: 690.3118

Example 6

6.1. Preparation of tris(1-n-butylimidazol-2-yl)phosphine

A solution of 4.97 g (40 mmol) of 1-n-butylimidazole in a mixture of 4.05 g (40 mmol) of triethylamine and 20 ml of pyridine was cooled to 0° C. and a solution of 1.83 g (13.3 mmol) of phosphorus trichloride in 5 ml of pyridine was slowly added dropwise. After the addition was complete, the mixture was brought to room temperature and then stirred for a further 14 hours at room temperature. The solvent was distilled off and the solid obtained in this way was extracted with warm benzene, filtered through silica gel and the extractant was subsequently distilled off. The oily residue obtained in this way was taken up in 20 ml of THF, admixed with 0.6 g (14.1 mmol) of lithium chloride and the mixture was stirred for a number of hours. The LiCl complex formed was filtered off on a frit, washed with cold tetrahydrofuran, dried in a high vacuum, suspended in $CH_2Cl_2$ and decomplexed by stirring with concentrated ammonia for one hour. The organic phase was filtered through a little silica gel, the solvent was distilled off and the solid was dried in a high vacuum. This gave 3.99 g (9.9 mmol) (74%) of tris(1-n-butylimidazol-2-yl)phosphine in the form of a colorless oil.

$^1$H-NMR (200 MHz, $CDCl_3$): δ=0.68 (t, $^3J$ (H,H)=7.2 Hz, 3H, H$^9$), 1.06 (sext, $^3J$ (H,H)=7.2 Hz, 2H, H$^8$), 1.25 (quint, $^3J$ (H,H)=7.4 Hz, 2H, H$^7$), 3.94 (dt, $^3J$ (H,H)=7.3 Hz, $^4J$ (P,H)=1.1 Hz, 2H, H$^6$), 6.99 (s(br), 1H, H$^5$), 7.07 (s(br), 1H, H$^4$).

$^{31}$P-NMR (81.01 MHz, $CDCl_3$): δ=−63.1.

MS (EI): m/e (%)=400 (47) [M]$^+$, 371 (5) [M-ethyl]$^+$, 277 (11) [M-butylimidazole]$^+$, 179 (9) [$C_{11}H_{19}N_2$]$^+$, 124 (97) [butylimidazole]$^+$, 97 (98) [$C_6H_{11}N_2$]$^+$, 82 (100) [$C_4H_6N_2$]$^+$, 68 (32) [imidazole]$^+$.

6.2. Preparation of trichlorotris(1-n-butylimidazol-2-yl)phosphinechromium(III)

A solution of 0.62 g (1.55 mmol) of tris(1-n-butylimidazol-2-yl)phosphine in 5 ml of dichloromethane was slowly added at room temperature to a solution of 0.46 g (1.22 mmol) of chromium(III) trichloride-tris(tetrahydrofuran) in 10 ml of dichloromethane while stirring. The solution obtained in this way was stirred at room temperature for 14 hours, the dichloromethane was distilled off and the residue was washed with tetrahydrofuran. The residue was recrystallized from dichloromethane/hexane. This gave 0.52 g (0.93 mmol, 76%) of trichlorotris(1-n-utylimidazol-2-yl)phosphinechromium(III) as a green solid.

$^1$H-NMR (200 MHz, $CD_2Cl_2$): δ=1.1 (m(br), −2.0-+3.5 ppm, 9 H, $CH_2CH_2CH_2CH_3$), 7.2 (m(br), 6.5-10 ppm, 1 H, H4), 13.9 (s(br), 10.5-20.5 ppm, 1 H, H5).

$^{31}$P-NMR (81.01 MHz, $CD_2Cl_2$): δ=6.3.

MS (FAB): m/e (%)=522 (100) [M−Cl]$^+$, 487 (42) [M−2Cl]$^+$.

MS (HR-FAB): $C_{21}H_{33}N_6PCr^{35}Cl^{37}Cl$ calc.: 524.1257 found: 524.1334 $C_{21}H_{33}N_6PCr^{35}Cl_2$ calc.: 522.1286 found: 522.1353

Example 7

7.1. Preparation of tris(1-n-butyl-4-phenylimidazol-2-yl)phosphine

A solution of 10 mmol of ethylhexylimidazole in 100 ml of diethyl ether was cooled to −40° C. and 4 ml of n-BuLi solution (2.5 M in hexane, 10 mmol) was added dropwise. After stirring at −40° C. for 1 hour, the solution was cooled to −78° C. and a solution of 3.33 mmol of phosphorus trichloride in 10 ml of diethyl ether was slowly added dropwise. After the addition was complete, the resulting suspension was stirred at −78° C. for another 2 hours, brought to room temperature and then stirred for a further 14 hours at room temperature. The reaction mixture obtained in this way was filtered and the pulverulent residue was washed with a number of portions of cold diethyl ether, dried in a high vacuum and recrystallized from ethanol. The solid obtained in this way was suspended in 100 ml of dichloromethane and stirred with 50 ml of concentrated ammonia for 1 hour. The organic phase was filtered through a thin layer of silica gel which was then washed with a number of portions of dichloromethane. The solvent was distilled off and the solid was dried in a high vacuum. This gave tris(1-n-butyl-4-phenylimidazol-2-yl)phosphine in a yield of 72%.

$^1$H-NMR (200 MHz, $CDCl_3$): δ=0.76 (m, 3H, H$^9$), 1.24 (m, 2H, H$^8$), 1.54 (m, 2H, H$^7$, 4.18 (t, $^3J$ (H,H)=7.5 Hz, 2H, H$^6$), 7.2-7.5 (m, 4H, H$^5$+H$^{aryl}$), 7.8 (m, 2H, H$^{aryl}$).

$^{31}$P-NMR (81.01 MHz, $CDCl_3$): δ=−60.4

MS (HR-FAB): m/e (%)=635 (100) [M+Li]$^+$;

7.2. Preparation of trichlorotris(1-n-butylphenylimidazol-2-yl)phosphinechromium(III)

0.088 g (0.14 mmol) of tris(1-n-butyl-4-phenylimidazolyl)phosphine were added at room temperature to a solution of 0.053 g (0.14 mmol) of chromium(III) trichloride-tris(tetrahydrofuran) in 25 ml of dichloromethane while stirring. The solution obtained in this way was stirred at room temperature for 12 hours, the dichloromethane was distilled off, the residue was washed with hexane and dried in a high vacuum. Trichlorotris(1-n-butyl-4-phenylimidazolyl)phosphinechromium(III) was obtained in quantitative yield as a green solid.

MS (FAB): m/e (%)=752 (9) [M−Cl]$^+$, 715 (28) [M−2Cl]$^+$.

MS (HR-FAB): $C_{39}H_{45}N_6PCr^{35}Cl$ calc. 715.2537 found 715.2521

Example 8

8.1. Preparation of tris(4(5)-tert-butylimidazol-2-yl)phosphine

A solution of 9.18 g (46.3 mmol) of 1-dimethoxymethyl-tert-butylimidazole in 100 ml of tetrahydrofuran was cooled to −40° C. and 18.5 ml of n-BuLi solution (2.5 M in hexane, 46.3 mmol) were added dropwise. After stirring at −40° C. for 1 hour, the solution was cooled to −78° C. and a solution of 2.12 g (15.4 mmol) of phosphorus trichloride in 10 ml of tetrahydrofuran was slowly added dropwise. After the addition was complete, the resulting suspension was stirred at −78° C. for another 2 hours, brought to room temperature and then stirred for a further 14 hours at room temperature. The solvent was distilled off from the reaction mixture obtained in this way, the residue was admixed with 100 ml of dichloromethane and then 50 ml of concentrated ammonia and was stirred until phase separation occurred. The organic phase was filtered through a thin layer of silica gel which was then washed with a number of portions of dichloromethane. The solid was distilled off and the residue was admixed with 100 ml of a 50:50 mixture of acetone/water. The product precipitated after 7 days as a fine white solid, and this was filtered off and dried under reduced pressure. This gave 2.33 g (5.8 mmol) (37.8% )of tris(4(5)-tert-butylimidazol-2-yl)phosphine.

$^1$H-NMR (300 MHz, MeOH-d4): δ=1.20 (bs, 9H, CH$_3$), 6.82 (bs, 1H, H4(5)).

$^{31}$P-NMR (121.5 MHz, MeOH-d4): δ=−70.4.

MS (EI): m/e (%)=400 (100) [M−H]$^+$, 385 (67) [M−CH$_3$]$^+$, 276 (23), 261 (25), 125 (22), 108 (9).

MS (HR-EI): calc. 400.2504 found 400.2531

8.2. Preparation of trichlorotris(4(5)-tert-butylimidazol-2-yl)phosphinechromium(III)

A solution of 0.36 g (0.8 mmol) of tris(4(5)-tert-butylimidazol-2-yl)phosphine in 25 ml of tetrahydrofuran was added at room temperature to a solution of 0.3 g (0.79 mmol) of chromium(III) trichloride-tris(tetrahydrofuran) in 10 ml of tetrahydrofuran while stirring. The solution obtained in this way was stirred at room temperature for 12 hours, the solvent was distilled off, the residue was washed with hexane and dried in a high vacuum. This gave 0.42 g (94%) of trichlorotris(1-n-butyl-4-phenylimidazolyl)phosphinechromium(III) as a green solid.

MS (FAB): m/e (%)=582 (12) [M+Na]$^+$, 522 (100) [M−Cl]$^+$, 487 (58) [M−2Cl]$^+$, 364 (19), 154 (68).

Examples 9-16

Polymerization

The amount (mg) indicated in Table 1 of catalyst was weighed into a 250 ml Schienk flask which had been baked and filled with nitrogen and the catalyst was suspended in 100 ml of toluene while stirring at room temperature. 1.0 ml of a 10% solution of methylaluminoxane in toluene (about 1.4 mmol of Al) was added and the mixture was stirred for a few minutes. Ethene was then passed over the solution for the time indicated in Table 1. After the introduction of gas had been completed, the Schienk flask was briefly flushed with nitrogen and the reaction mixture was admixed with a solution of concentrated hydrochloric acid in methanol in a ratio of 1:2 to hydrolyze it. The polymer obtained in this way was filtered off, washed a number of times with methanolic hydrochloric acid and dried at 110° C. for 12 hours in a drying oven and then weighed. To characterize the product, the melting point, mass and C/H ratio are determined. The organic phase is dried over sodium sulfate and analyzed for low molecular weight polymer components on a gas chromatograph/mass spectrometer.

The filtrate from the polymer filtration was analyzed for low molecular weight polymer constituents by means of GC-MS measurements. The GC-MS-analyses of the filtrates gave no indication of low molecular weight polymer products or cyclotrimers such as cyclohexane.

TABLE 1

Polymerization results

| Ex. | Cat. from Ex. | Amount of cat. [mg] ([μmol]) | t(poly) [h] | Polymer [g] | M.p.$^{a)}$ [° C.] | Prod. [g/(mmol M·h)] |
|---|---|---|---|---|---|---|
| 9 | 1 | 9.0 (13.7) | 1 | 0.82 | — | 61 |
| 10 | 2 | 2.2 (2.27) | 0.5 | 1.50 | — | 986 |
| 11 | 3 | 3.4 (5.15) | 0.67 | 0.16 | — | 47 |
| 12 | 4 | 5.0 (7.6) | 1 | 0.33 | 140-150 | 44 |
| 13 | 5 | 3.7 (5.08) | 0.83 | 0.27 | 138 | 64 |
| 14 | 6 | 3.1 (5.5) | 0.87 | 1.93 | 142-144 | 400 |
| 15 | 7 | 4.2 (5.3) | 1 | 0.27 | — | 51 |
| 16 | 8 | 6.4 (1.15) | 0.93 | 0.54 | 134 | 50 |

$^{a)}$Melting points were determined using a Büchi instrument

Examples 17-19

Polymerization

The polymerizations were carried out at 40° C. under argon in a 1 l four-necked flask provided with contact thermometer, stirrer with Teflon blade, heating mantle and gas inlet tube. The appropriate amount of MAO (10% strength solution in toluene, Cr:Al corresponding to Table 2) were added to a solution of the amount indicated in Table 2 of the appropriate complex in 250 ml of toluene and the mixture was heated to 40° C. on a waterbath. In the case of the copolymerization in Example 19, 3 ml of hexene were added shortly before the introduction of ethylene. Ethylene was then passed through the mixture at a flow rate of from about 20 to 40 l/h at atmospheric pressure. After 1 hour under a constant flow of ethylene, the polymerization was stopped by addition of methanolic HCl solution (15 ml of concentrated hydrochloric acid in 50 ml of methanol). 250 ml of methanol were subsequently added and the resulting white polymer was filtered off, washed with methanol and dried at 70° C.

TABLE 2

Polymerization results

| Ex. | Cat. from Ex. | Amount of cat. [mg] ([mmol]) | Cr:Al | Polymer [g] | Prod. [g/(mmol M · h)] | $M_w$ [g/mol] | $M_w/M_n$ | Eta value [dl/g] | DSC [° C.] | CH$^3$/1000 C. | Density [g/cm$^3$] |
|---|---|---|---|---|---|---|---|---|---|---|---|
| 17 | 4 | 18.8 (28.4) | 1:750 | 1.01 | 36 | 403737 | — | 3.8 | 134.8 | 6 | — |
| 18 | 6 | 15 (26.4) | 1:500 | 8.5 | 322 | 617960 | 31.2 | 5.5 | 137.5 | 1.5 | 0.9567 |
| 19 | 6 | 28 (49.3) | 1:240 | 5.2 | 105 | — | — | — | — | — | — |

We claim:

1. A transition metal complex comprising formula $(Z^A)M^AX_k$ (V), wherein:
    $M^A$ is a transition metal of group 3 or 4 of the Periodic Table of Elements;
    $Z^A$ is a ligand of formula (IV)

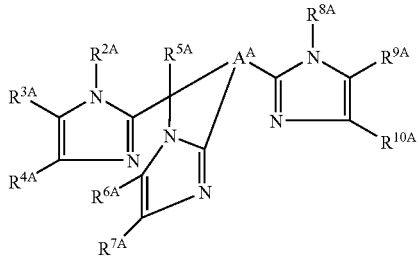

wherein
    $A^A$ is P;
    $R^{2A}$- $R^{10A}$ are each, independently of one another, hydrogen, $C_1$-$C_{20}$-alkyl, $C_2$-$C_{20}$-alkenyl, $C_6$-$C_{20}$-aryl, alkylaryl comprising from 1 to 10 carbon atoms in the alkyl part and 6-20 carbon atoms in the aryl part, $NR^{11A}{}_2$, $N(SiR^{11A}{}_3)_2$, $OR^{11A}$, $OSiR^{11A}{}_3$, $SiR^{11A}{}_3$ or halogen, wherein the organic radicals $R^{2A}$-$R^{10A}$ may also be substituted by halogens and two vicinal radicals $R^{2A}$-$R^{10A}$ may also be joined to form a five- or six-membered ring, and/or two vicinal radicals $R^{2A}$-$R^{10A}$ may be joined to form a heterocycle containing at least one atom from the group consisting of N, P, O or S;
    $R^{11A}$ are each, independently of one another, hydrogen, $C_1$-$C_{20}$-alkyl, $C_2$-$C_{20}$-alkenyl, $C_6$-$C_{20}$-aryl, alkylaryl comprising from 1 to 10 carbon atoms in the alkyl part and 6-20 carbon atoms in the aryl part and two geminal radicals $R^{11A}$ may also be joined to form a five- or six-membered ring;
    $R^{1X}$-$R^{2X}$ are each, independently of one another, hydrogen, $C_1$-$C_{20}$-alkyl, $C_2$-$C_{20}$-alkenyl, $C_6$-$C_{20}$-aryl, alkylaryl comprising from 1 to 10 carbon atoms in the alkyl part and 6-20 carbon atoms in the aryl part or $SiR^{3X}{}_3$, wherein the organic radicals $R^{1X}$-$R^{2X}$ may also be substituted by halogens or nitrogen- and oxygen-containing groups and two radicals $R^{1X}$-$R^{2X}$ may also be joined to form a five- or six-membered ring;
    $R^{3X}$ are each, independently of one another, hydrogen, $C_1$-$C_{20}$-alkyl, $C_2$-$C_{20}$-alkenyl, $C_6$-$C_{20}$-aryl, alkylaryl comprising from 1 to 10 carbon atoms in the alkyl part and 6-20 carbon atoms in the aryl part and two radicals $R^{3X}$ may also be joined to form a five- or six-membered ring;
    X are each, independently of one another, fluorine, chlorine, bromine, iodine, hydrogen, $C_1$-$C_{10}$-alkyl, $C_2$-$C_{10}$alkenyl, $C_6$-$C_{20}$-aryl, alkylaryl comprising 1-10 carbon atoms in the alkyl part and 6-20 carbon atoms in the aryl part, $NR^{1X}R^{2X}$, $OR^{1X}$, $SR^{1X}$, $SO_3R^{1X}$, $OC(O)R^{1X}$, CN, SCN, β-diketonate, CO, $BF_4{}^-$, $PF_6{}^-$ or a bulky noncoordinating anion; and
    k is 1, 2, or 3.

2. A transition metal complex comprising formula $(Z^A)M^A$ (III), wherein:
    $M^A$ is a transition metal of group 3 or 4 of the Periodic Table of Elements;
    $Z^A$ is a ligand of formula (IV)

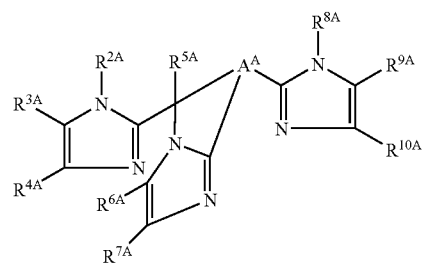

wherein
    $A^A$ is P,
    $R^{2A}$-$R^{10A}$ are each, independently of one another, hydrogen, $C_1$-$C_{20}$-alkyl, $C_2$-$C_{20}$-alkenyl, $C_6$-$C_{20}$-aryl, alkylaryl comprising from 1 to 10 carbon atoms in the alkyl part and 6-20 carbon atoms in the aryl part, $NR^{11A}{}_2$, $N(SiR^{11A}{}_3)_2$, $OR^{11A}$, $OSiR^{11A}{}_3$, $SiR^{11A}{}_3$ or halogen, wherein the organic radicals $R^{2A}$-$R^{10A}$ may also be substituted by halogens and two vicinal radicals $R^{2A}$-$R^{10A}$ may also be joined to form a five- or six-membered ring, and/or two vicinal radicals $R^{2A}$-$R^{10A}$ may be joined to form a heterocycle containing at least one atom from the group consisting of N, P, O or S; and
    $R^{11A}$ are each, independently of one another, hydrogen, $C_1$-$C_{20}$-alkyl, $C_2$-$C_{20}$-alkenyl, $C_6$-$C_{20}$-aryl, alkylaryl comprising from 1 to 10 carbon atoms in the alkyl part and 6-20 carbon atoms in the aryl part and two geminal radicals $R^{11A}$ may also be joined to form a five- or six-membered ring.

3. The transition metal complex as claimed in claim 1, wherein:
    $R^{2A}$, $R^{5A}$ and $R^{8A}$ are the same;
    $R^{3A}$, $R^{6A}$ and $R^{9A}$ are the same; and
    $R^{4A}$, $R^{7A}$ and $R^{10A}$ are the same.

4. The transition metal complex as claimed in claim 2, wherein:
    $R^{2A}$, $R^{5A}$ and $R^{8A}$ are the same;
    $R^{3A}$, $R^{6A}$ and $R^{9A}$ are the same; and
    $R^{4A}$, $R^{7A}$ and $R^{10A}$ are the same.

5. A catalyst system for olefin polymerization comprising:
    A) at least one transition metal complex comprising formula $(Z^A)M^AX_k$ (V), wherein:
    $M^A$ is a transition metal of group 3 or 4 of the Periodic Table of Elements;
    $Z^A$ is a ligand of formula (IV)

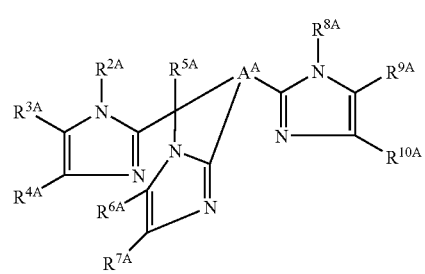

wherein $A^A$ is P;

$R^{2A}$-$R^{10A}$ are each, independently of one another, hydrogen, $C_1$-$C_{20}$-alkyl, $C_2$-$C_{20}$-alkenyl, $C_6$-$C_{20}$-aryl, alkylaryl comprising from 1 to 10 carbon atoms in the alkyl part and 6-20 carbon atoms in the aryl part, $NR^{11A}_2$, $N(SiR^{11A}_3)_2$, $OR^{11A}$, $OSiR^{11A}_3$, $SiR^{11A}_3$ or halogen, wherein the organic radicals $R^{2A}$-$R^{10A}$ may also be substituted by halogens and two vicinal radicals $R^{2A}$-$R^{10A}$ may also be joined to form a five- or six-membered ring, and/or two vicinal radicals $R^{2A}$-$R^{10A}$ may be joined to form a heterocycle containing at least one atom from the group consisting of N, P, O or S;

$R^{11A}$ are each, independently of one another, hydrogen, $C_1$-$C_{20}$-alkyl, $C_2$-$C_{20}$-alkenyl, $C_6$-$C_{20}$-aryl, alkylaryl comprising from 1 to 10 carbon atoms in the alkyl part and 6-20 carbon atoms in the aryl part and two geminal radicals $R^{11A}$ may also be joined to form a five- or six-membered ring;

$R^{1X}$-$R^{2X}$ are each, independently of one another, hydrogen, $C_1$-$C_{20}$-alkyl, $C_2$-$C_{20}$-alkenyl, $C_6$-$C_{20}$-aryl, alkylaryl comprising from 1 to 10 carbon atoms in the alkyl part and 6-20 carbon atoms in the aryl part or $SiR^{3X}_3$, wherein the organic radicals $R^{1X}$-$R^{2X}$ may also be substituted by halogens or nitrogen- and oxygen-containing groups and two radicals $R^{1X}$-$R^{2X}$ may also be joined to form a five- or six-membered ring;

$R^{3X}$ are each, independently of one another, hydrogen, $C_1$-$C_{20}$-alkyl, $C_2$-$C_{20}$-alkenyl, $C_6$-$C_{20}$-aryl, alkylaryl comprising from 1 to 10 carbon atoms in the alkyl part and 6-20 carbon atoms in the aryl part and two radicals $R^{3X}$ may also be joined to form a five- or six-membered ring;

X are each, independently of one another, fluorine, chlorine, bromine, iodine, hydrogen, $C_1$-$C_{10}$-alkyl, $C_2$-$C_{10}$-alkenyl, $C_6$-$C_{20}$-aryl, alkylaryl comprising 1-10 carbon atoms in the alkyl part and 6-20 carbon atoms in the aryl part, $NR^{1X}R^{2X}$, $OR^{1X}$, $SR^{1X}$, $SO_3R^{1X}$, $OC(O)R^{1X}$, CN, SCN, β-diketonate, CC, $BF_4^-$, $PF_6^-$ or a bulky noncoordinating anion; and K is 1, 2, or 3;

B) optionally, an organic or inorganic support;
C) optionally, one or more activating compounds;
D) optionally, further catalysts suitable for olefin polymerization; and
E) optionally, one or more metal compounds of group 1, 2 or 13 of the Periodic Table.

6. A catalyst system for olefin polymerization comprising:
A) at least one transition metal complex comprising formula $(Z^A)M^A$ (III), wherein:
$M^A$ is a transition metal of group 3 or 4 of the Periodic Table of Elements;
$Z^A$ is a ligand of formula (IV)

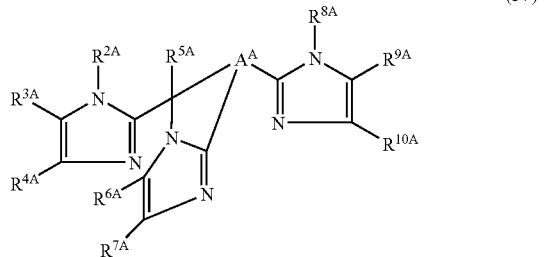

(IV)

wherein
$A^A$ is P, $R^{2A}$-$R^{10A}$ are each, independently of one another, hydrogen, $C_1$-$C_{20}$-alkyl, $C_2$-$C_{20}$-alkenyl, $C_6$-$C_{20}$-aryl, alkylaryl comprising from 1 to 10 carbon atoms in the alkyl part and 6-20 carbon atoms in the aryl part, $NR^{11A}_2$, $N(SiR^{11A}_3)_2$, $OR^{11A}$, $OSiR^{11A}_3$, $SiR^{11A}_3$ or halogen, wherein the organic radicals $R^{2A}$-$R^{10A}$ may also be substituted by halogens and two vicinal radicals $R^{2A}$-$R^{10A}$ may also be joined to form a five- or six-membered ring, and/or two vicinal radicals $R^{2A}$-$R^{10A}$ may be joined to form a heterocycle containing at least one atom from the group consisting of N, P, O or S; and $R^{11A}$ are each, independently of one another, hydrogen, $C_1$-$C_{20}$-alkyl, $C_2$-$C_{20}$-alkenyl, $C_6$-$C_{20}$-aryl, alkylaryl comprising from 1 to 10 carbon atoms in the alkyl part and 6-20 carbon atoms in the aryl part and two geminal radicals $R^{11A}$ may also be joined to form a five- or six-membered ring;

B) optionally, an organic or inorganic support;
C) optionally, one or more activating compounds;
D) optionally, further catalysts suitable for olefin polymerization; and
E) optionally, one or more metal compounds of group 1, 2 or 13 of the Periodic Table.

7. A prepolymerized catalyst system comprising the catalyst system as claimed in claim 5, further comprising at least one linear $C_2$-$C_{10}$-1-alkene polymerized onto the catalyst system in a mass ratio of from 1:0.1 to 1:1000, based on the catalyst system.

8. A prepolymerized catalyst system comprising the catalyst system as claimed in claim 6, further comprising at least one linear $C_2$-$C_{10}$-1-alkene polymerized onto the catalyst system in a mass ratio of from 1:0.1 to 1:1000, based on the catalyst system.

9. A process for polymerizing or copolymerizing least one olefin in presence of a catalyst system to produce at least one polymer, the catalyst system comprising at least one transition metal complex comprising formula $(Z^A)M^AX_k$ (V), wherein:
$M^A$ is a transition metal of group 3 or 4 of the Periodic Table of Elements;
$Z^A$ is a ligand of the formula (IV)

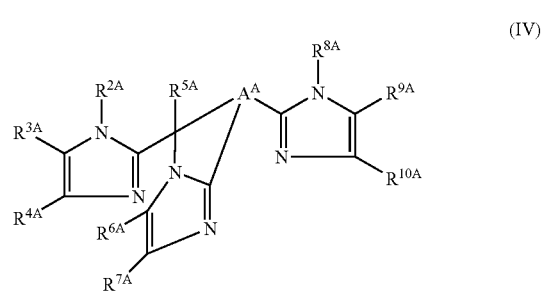

(IV)

wherein
$A^A$ is P;

$R^{2A}$-$R^{10A}$ are each, independently of one another, hydrogen, $C_1$-$C_{20}$-alkyl, $C_2$-$C_{20}$-alkenyl, $C_6$-$C_{20}$-aryl, alkylaryl comprising from 1 to 10 carbon atoms in the alkyl part and 6-20 carbon atoms in the aryl part, $NR^{11A}_2$, $N(SiR^{11A}_3)_2$, $OR^{11A}$, $OSiR^{11A}_3$, $SiR^{11A}_3$ or halogen, wherein the organic radicals $R^{2A}$-$R^{10A}$ may also be substituted by halogens and two vicinal radicals $R^{2A}$-$R^{10A}$ may also be joined to form a five- or six-membered ring, and/or two vicinal radicals $R^{2A}$-$R^{10A}$ may be joined to form a heterocycle containing at least one atom from the group consisting of N, P, O or S;

$R^{11A}$ are each, independently of one another, hydrogen, $C_1$-$C_{20}$-alkyl, $C_2$-$C_{20}$-alkenyl, $C_6$-$C_{20}$-aryl, alkylaryl comprising from 1 to 10 carbon atoms in the alkyl part and 6-20 carbon atoms in the aryl part and two geminal radicals $R^{11A}$ may also be joined to form a five- or six-membered ring;

$R^{1X}$-$R^{2X}$ are each, independently of one another, hydrogen, $C_1$-$C_{20}$-alkyl, $C_2$-$C_{20}$-alkenyl, $C_6$-$C_{20}$-aryl, alkylaryl comprising from 1 to 10 carbon atoms in the alkyl part and 6-20 carbon atoms in the aryl part or $SiR^{3X}_3$, wherein the organic radicals $R^{1X}$-$R^{2X}$ may also be substituted by halogens or nitrogen- and oxygen-containing groups and two radicals $R^{1X}$-$R^{2X}$ may also be joined to form a five- or six-membered ring;

$R^3$ are each, independently of one another, hydrogen, $C_1$-$C_{20}$-alkyl, $C_2$-$C_{20}$-alkenyl, $C_6$-$C_{20}$-aryl, alkylaryl comprising from 1 to 10 carbon atoms in the alkyl part and 6-20 carbon atoms in the aryl part and two radicals $R^{3X}$ may also be joined to form a five- or six-membered ring;

X are each, independently of one another, fluorine, chlorine, bromine, iodine, hydrogen, $C_1$-$C_{10}$-alkyl, $C_2$-$C_{10}$-alkenyl, $C_6$-$C_{20}$-aryl, alkylaryl comprising 1-10 carbon atoms in the alkyl part and 6-20 carbon atoms in the aryl part, $NR^{1X}R^{2X}$, $OR^{1X}$, $SR^{1X}$, $SO_3R^{1X}$, $OC(O)R^{1X}$, CN, SCN, β-diketonate, CO, $BF_4^{31}$, $PF_6^{31}$ or a bulky non-coordinating anion; and k is 1, 2, or 3.

10. A process for polymerizing or copolymerizing at least one olefin in presence of a catalyst system to produce at least one polymer, the catalyst system comprising at least one transition metal complex comprising formula $(Z^A)M^A$ (III), wherein:

$M^A$ is a transition metal of group 3 or 4 of the Periodic Table of Elements;

$Z^A$ is a ligand of the formula (IV)

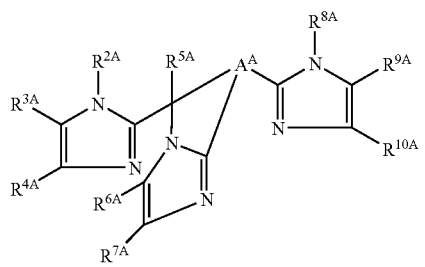

(IV)

wherein $A^A$ is P, $R^{2A}$-$R^{10A}$ are each, independently of one another, hydrogen, $C_1$-$C_{20}$-alkyl, $C_2C_{20}$-alkenyl, $C_6$-$C_{20}$-aryl, alkylaryl comprising from 1 to 10 carbon atoms in the alkyl part and 6-20 carbon atoms in the aryl part, $NR^{11A}_2$, $N(SiR^{11A}_3)_2$, $OR^{11A}$, $OSiR^{11A}_3$, $SiR^{11A}_3$ or halogen, wherein the organic radicals $R^{2A}$-$R^{10A}$ may also be substituted by halogens and two vicinal radicals $R^{2A}$-$R^{10A}$ may also be joined to form a five- or six-membered ring, and/or two vicinal radicals $R^{2A}$-$R^{10A}$ may be joined to form a heterocycle containing at least one atom from the group consisting of N, P, O or S; and $R^{11A}$ are each, independently of one another, hydrogen, $C_1$-$C_{20}$alkyl, $C_2$-$C_{20}$-alkenyl, $C_6$-$C_{20}$-aryl, alkylaryl comprising from 1 to 10 carbon atoms in the alkyl part and 6-20 carbon atoms in the aryl part and two geminal radicals $R^{11A}$ may also be joined to form a five- or six-membered ring.

11. The process as claimed in claim 9, wherein the at least one olefin is selected from ethene, propene, 1-butene, 1-pentene, 1-hexene, 1-heptene, 1-octene, 1-decene, norbornene, and mixtures thereof.

12. The process as claimed in claim 10, wherein the at least one olefin is selected from ethene, propene, 1-butene, 1-pentene, 1-hexene, 1-heptene, 1-octene, 1-decene, norbornene, and mixtures thereof.

13. The process as claimed in claim 9, wherein the process comprises a monomer mixture of at least 50 mol % of ethene.

14. The process as claimed in claim 10, wherein the process comprises a monomer mixture of at least 50 mol % of ethene.

15. The process as claimed in claim 9, wherein the process comprises polymerizing propene.

16. The process as claimed in claim 10, wherein the process comprises polymerizing propene.

17. The process as claimed in claim 15, wherein the process further comprises polymerizing ethene, butane, and mixtures thereof.

18. The process as claimed in claim 16, wherein the process further comprises polymerizing ethene, butane, and mixtures thereof.

19. The process as claimed in claim 9, wherein the polymer is an ethylene-containing polymer.

20. The process as claimed in claim 10 wherein the polymer is an ethylene-containing polymer.

21. A transition metal complex comprising formula $(Z^A)$ $M^A$ (III), wherein:

$M^A$ is vanadium or chromium; and $Z^A$ is a ligand of the formula (IV)

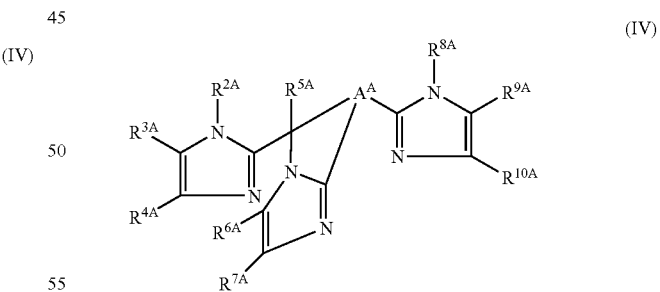

(IV)

wherein $A^A$ is P, $R^{2A}$, $R^{5A}$ and $R^{8A}$ are each a linear or branched $C_1$-$C_{20}$-alkyl group;

$R^{3A}$, $R^{4A}$, $R^{6A}$, $R^{7A}$, $R^{9A}$, and $R^{10A}$ are each, independently of one another, hydrogen, $C_1$-$C_{20}$-alkyl, $C_2$-$C_{20}$-alkenyl, $C_6$-$C_{20}$-aryl, alkylaryl comprising from 1 to 10 carbon atoms in the alkyl part and 6-20 carbon atoms in the aryl part, $NR^{11A}_2$, $N(SiR^{11A}_3)_2$, $OR^{11A}$, $OSiR^{11A}_3$, $SIR^{11A}_3$ or halogen, wherein the organic radicals $R^{2A}$-$R^{10A}$ may also be substituted by halogens and two vicinal radicals $R^{2A}$-$R^{10A}$ may also be joined to form a five- or six-membered ring, and/or two vicinal radicals $R^{2A}$-$R^{10A}$ may be joined to form a heterocycle containing at least one atom from the group consisting of N, P, O or S, with the proviso that at least one of $R^{4A}$, $R^{7A}$, and $R^{10A}$ is hydrogen; and $R^{11A}$ are each, independently of one another, hydrogen, $C_1$-$C_{20}$-alkyl, $C_2$-$C_{20}$-alkenyl, $C_6$-$C_{20}$-aryl, alkylaryl comprising from 1 to 10 carbon atoms in the alkyl part and 6-20 carbon atoms in the aryl part and two geminal radicals $R^{11A}$ may also be joined to form a five- or six-membered ring.

* * * * *